(12) United States Patent
Soldatov et al.

(10) Patent No.: US 8,999,677 B1
(45) Date of Patent: *Apr. 7, 2015

(54) METHOD FOR DIFFERENTIATION OF POLYNUCLEOTIDE STRANDS

(71) Applicant: Max-Planck-Gesellschaft zur Forderung der Wissenschaften e.V., München (DE)

(72) Inventors: Aleksey Soldatov, Berlin (DE); Tatiana Borodina, Berlin (DE); Hans Lehrach, Berlin (DE)

(73) Assignee: Max-Planck Gesellschaft zur Förderung der Wissenschaften e.V., München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/546,844

(22) Filed: Nov. 18, 2014

Related U.S. Application Data

(63) Continuation of application No. 13/382,673, filed as application No. PCT/EP2010/004399 on Jul. 6, 2010.

(60) Provisional application No. 61/213,730, filed on Jul. 8, 2009.

(30) Foreign Application Priority Data

Jul. 6, 2009 (EP) .................................... 09008808

(51) Int. Cl.
*C12P 19/34* (2006.01)
*C12Q 1/68* (2006.01)

(52) U.S. Cl.
CPC ............ *C12Q 1/6848* (2013.01); *C12Q 1/6855* (2013.01)

(58) Field of Classification Search
CPC ........................ C12Q 1/6853; C12Q 2525/117
USPC ................................................. 435/91.2, 6.1
See application file for complete search history.

(56) References Cited

U.S. PATENT DOCUMENTS

| | | | |
|---|---|---|---|
| 5,418,149 | A | 5/1995 | Gelfand et al. |
| 7,413,857 | B2 | 8/2008 | Dahl et al. |
| 2005/0136417 | A1 | 6/2005 | Cole et al. |
| 2006/0141498 | A1 | 6/2006 | Wu et al. |
| 2007/0281863 | A1 | 12/2007 | Rabbani et al. |
| 2010/0297709 | A1 | 11/2010 | Rashtchian |

FOREIGN PATENT DOCUMENTS

| | | |
|---|---|---|
| WO | WO03008538 | 1/2003 |
| WO | WO2009006438 | 1/2009 |

OTHER PUBLICATIONS

Parkhomchuk, et al., "Transcriptome analysis by strand-specific sequencing of complementary DNA", Nucleic Acids Research, 2009, vol. 37, No. 18. e123, 7 pages.

*Primary Examiner* — Cynthia B Wilder
(74) *Attorney, Agent, or Firm* — James S. Keddie; Bozicevic, Field & Francis, LLP

(57) ABSTRACT

Objective of the present invention is to provide a method for keeping of directional information in double-stranded DNA. We suggest to convert polynucleotide into a hybrid double-stranded DNA. One particular strand of this hybrid double-stranded DNA should be synthesized using at least one modified nucleotide. Thus, this particular strand would contain modified nucleotides along the whole length. Density of directional markers would not depend on the length of polynucleotides. Any internal fragments of the hybrid double-stranded DNA would have directional information. When it is necessary the modified strand may be easily degraded or separated from the other strand. It was found that such hybrid double-stranded DNA may be easily generated in a number of molecular biology tasks and may be used for molecular cloning, library preparation and strand separation.

13 Claims, 18 Drawing Sheets

Figure 5 (Con't)

Adaptor ligation

Figure 1:
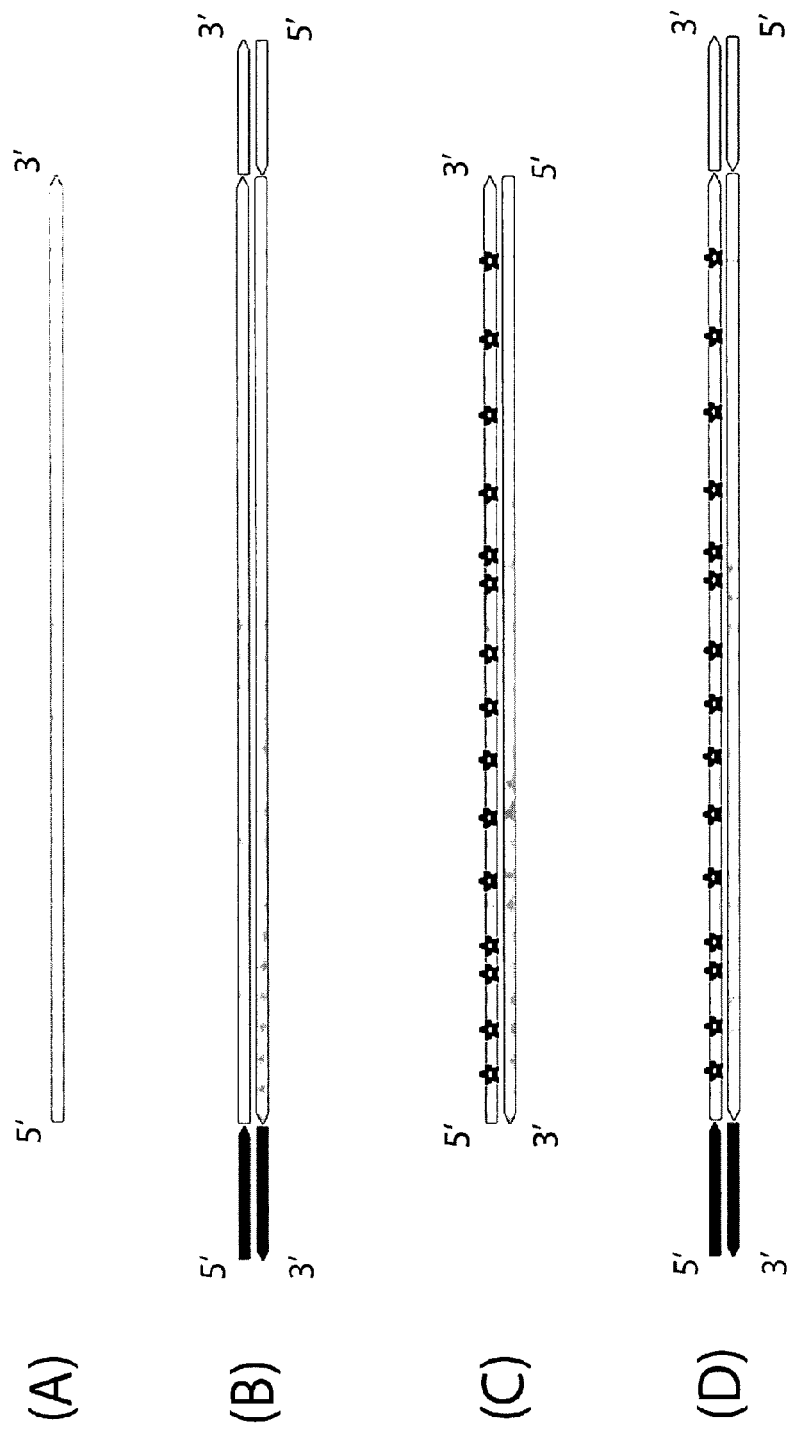

Fragment_A:

```
           #Ad_1                                                                                    #Ad_2
5' TACACTCTTTCCCTACACGAC                                                              TCGTATGCCGTCTTCTGCTTG 3'   (SEQ ID. NO:18)
                      GCTCTTCCGATCT nUnnnnnnUUnnnnUnnnUnnnnnnUUnnnnnnUnnnnA GATCGGAAGAGC
                      CGAGAAGGCTAG AnAnnnnnnAAnnAnnnnnnAnnnnnnAAmnnmNNNNN TCTAGCCTTCTCG
3' GTTCGTCTTCGCCGTATGCT                                                              CAGCACATCCCTTCTCACAT 5'    (SEQ ID. NO:19)
           #Ad_2                                                                                    #Ad_1
```

Fragment_B:

```
           #Ad_1                                                                                    #Ad_2
5' TACACTCTTTCCCTACACGAC                                                              TCGTATGCCGTCTTCTGCTTG 3'   (SEQ ID. NO:20)
                      GCTCTTCCGATCT nnUnnnnnnnUUUnnnUnnUnnAAAAAAAAAAAAAAAA GATCGGAAGAGC
                      CGAGAAGGCTAG AnnAnnnnnnnAAAnnnnnnnnAAnnnAnnnAnnTTTTTTTTTTTTTTTT TCTAGCCTTCTCG
3' GTTCGTCTTCGCCGTATGCT                                                              CAGCACATCCCTTTCTCACAT 5'   (SEQ ID. NO:21)
           #Ad_2                                                                                    #Ad_1
```

UDGase treatment

Fragment_A:

```
           #Ad_1                                                                                    #Ad_2
     SEQ ID. NO:22)                 (SEQ ID. No:24) (SEQ ID. No:26)
5' TACACTCTTTCCCTACACGAC     (SEQ ID. NO:23)   (SEQ ID. NO:25)          (SEQ ID. NO:27)   TCGTATGCCGTCTTCTGCTTG 3'
                      GCTCTTCCGATCT n·nnnnnn··nnnn·nnn·nnnrnn··nnnnnnnnnnA GATCGGAAGAGC
                      CGAGAAGGCTAG AnAnnnnnnAAnnAnnnnnnAnnnnnnAAmnnmNNNNN TCTAGCCTTCTCG
3' GTTCGTCTTCGCCGTATGCT                                                              CAGCACATCCCTTCTCACAT 5'    (SEQ ID. NO:19)
           #Ad_2                                                                                    #Ad_1
```

Fragment_B:

```
           #Ad_1                        (SEQ ID. No:30)     (SEQ ID. No:32)
                     (SEQ ID. No:28)              (SEQ ID. No:29)      (SEQ ID. No:31)
5' TACACTCTTTCCCTACACGAC                                                              TCGTATGCCGTCTTCTGCTTG 3'
                      GCTCTTCCGATCT nn·nnnnhnnn··nnnn·nh·nnAAAAAAAAAAAAAAAA GATCGGAAGAGC
                      CGAGAAGGCTAG AnnAnnnnnnnAAAnnnnnnnnAAnnnAnnnAnnTTTTTTTTTTTTTTTT TCTAGCCTTCTCG
3' GTTCGTCTTCGCCGTATGCT                                                              CAGCACATCCCTTTCTCACAT 5'   (SEQ ID. NO:21)
           #Ad_2                                                                                    #Ad_1
```

Figure 5 (con't)

Preamplification

Fragment_A:

```
                      #PCR_2                                                                    #PCR_1
5' CAAGCAGAAGACGGCATACGAGCTCTTCCGATCT 3'        (SEQ ID. No:33)     3' TCTAGCCTTCTCGCAGCACATCCCTTTCTCACATCTAGAGCCACCAGGGCATAGTAA 5'  (SEQ ID. No:34)
   |<--------- 34bp ---------------->|<                50-150bp                        58bp                                       >|
3' GTTCGTCTTCTGCGCCGTATGCTCGAGAAGGCTAGAAAnnnnnnAAnnnnnnnAnnnAnnnnnnnnNNNNNNTCTAGCCTTCTCGCAGCACATCCCTTTCTCACAT 5'                    (SEQ ID. No:19)
         #Ad_2                                                         #Ad_1
```

Fragment_B:

```
3' GTTCGTCTTCTGCGCCGTATGCTCGAGAAGGCTAGAnnAnnnnnnnAAAnnnnnnnAAnnnAnnnAnnTTTTTTTTTTTTTTTTCTAGCCTTCTCGCAGCACATCCCTTTCTCACAT 5'     (SEQ ID. No:21)
         #Ad_2                                                                                                  #Ad_1
```

FlowCell preparation

Amplification

Fragment_A:

```
5' CAAGCAGAAGACGGCATACGAGCTCTTCCGATCTnTnnnnnTnnTnnnnnnnnAGATCGGAAGAGCGTCGTGTAGGGAAAGAGTGTAGATCTCGGTGGTCGCCGTATCATT 3'  (SEQ ID. No:35)
3' GTTCGTCTTCTGCCGTATGCTCGAGAAGGCTAGAnAnnnnnnAnAnnnnnnNNNNNNNTCTAGCCTTCTCCAGCACATCCCTTCTCACATCTAGAGCCGCCAGTAGCGGCATAGTAA 5'  (SEQ ID. No:36)
```

Fragment_B:

```
5' CAAGCAGAAGACGGCATACGAGCTCTTCCGATCTnnTnnnTnnnnnnnnnTTTnnnnTTnnnnTTnnAAAAAAAAAAAAAAAAAGATCGGAAGAGCGTCGTGTAGGGAAAGAGTGTAGATCTCGGTGGTCGCCGTATCATT 3'  (SEQ ID. No:37)
3' GTTCGTCTTCTGCCGTATGCTCGAGAAGGCTAGAnnAnnnnnnAAAnnnnnnnnnAAnnAnnnAnnTTTTTTTTTTTTTTTTTCTAGCCTTCTCGCAGCACATCCCTTCTCACATCTAGAGCCACCAGCGGCATAGTAA 5'  (SEQ ID. No:38)
```

Linearisation

Fragment_A:

```
5' CAAGCAGAAGACGGCATACGAGCTCTTCCGATCTnTnnnnnTnnTnnnnnnnnAGATCGGAAGAGCGTCGTGTAGGGAAAGAGTGTAGATCTCGGTGGTCGCCGTATCATT 3'  (SEQ ID. No:35)
```

Fragment_B:

```
5' CAAGCAGAAGACGGCATACGAGCTCTTCCGATCTnnTnnnTnnnnnnnnnTTTnnnnTTnnnnTnnTnnAAAAAAAAAAAAAAAAAGATCGGAAGAGCGTCGTGTAGGGAAAGAGTGTAGATCTCGGTGGTCGCCGTATCATT 3'  (SEQ ID. No:37)
```

Figure 5 (Con't)

Sequencing primer annealing

Fragment_A:

```
                                                                                 sequencing primer
                                                          <----  3' TCTAGCCTTCTCGCAGCACATCCCTTTCTCACA 5'                                           (SEQ ID NO:39)
                                                                  ||||||||||||||||||||||||||||||||||
5' CAAGCAGAAGACGGCATACGAGCTCTTCCGATCTnTnnnnnnnTnnnTnnnnnnTTnnnnnnAGATCGGAAGAGCGTCGTGTAGGGAAAGAGTGTAGATCTCGGTGGTCGCCGTATCATT 3'  (SEQ ID NO:35)
```

Fragment_B:

```
                                                                              <----  3' TCTAGCCTTCTCGCAGCACATCCCTTTCTCACA 5'                                            (SEQ ID NO:39)
                                                                                        ||||||||||||||||||||||||||||||||||
5' CAAGCAGAAGACGGCATACGAGCTCTTCCGATCTnnTnnnnnnnnTTTnnnnTnnTnnAAAAAAAAAAAAAAAAAAAGATCGGAAGAGCGTCGTGTAGGGAAAGAGTAGATCTCGGTGGTCGCCGTATCATT   (SEQ ID NO:37)
```

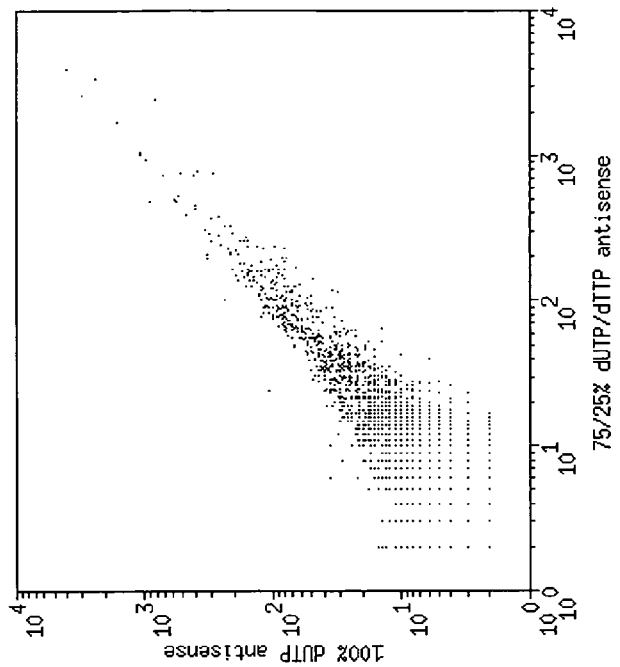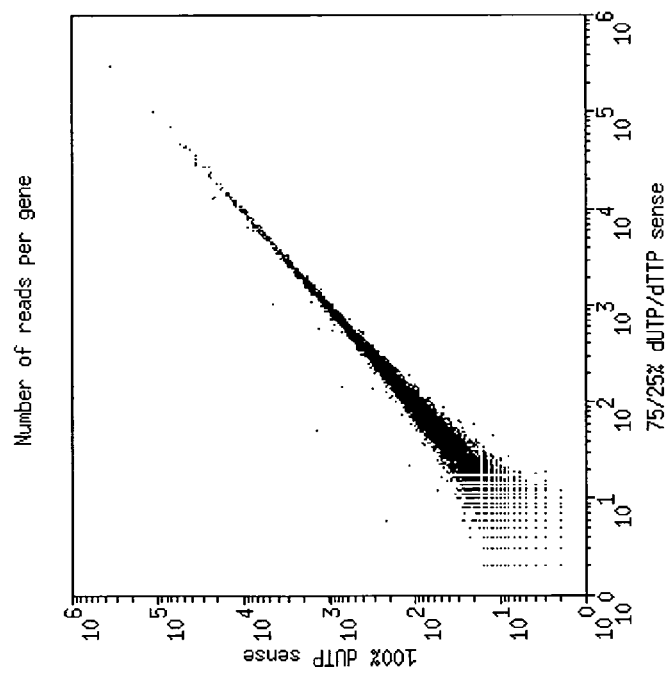
Figure 8

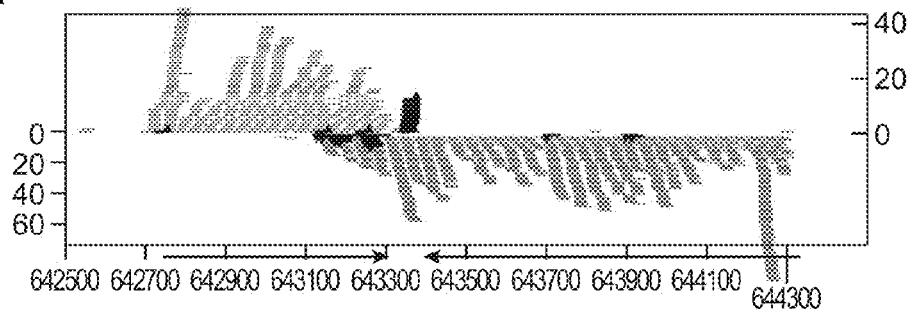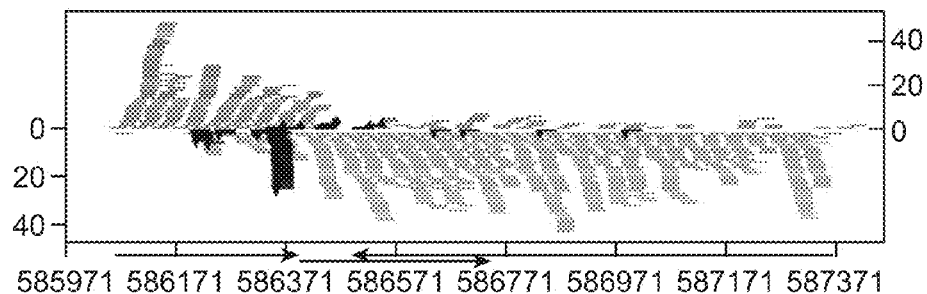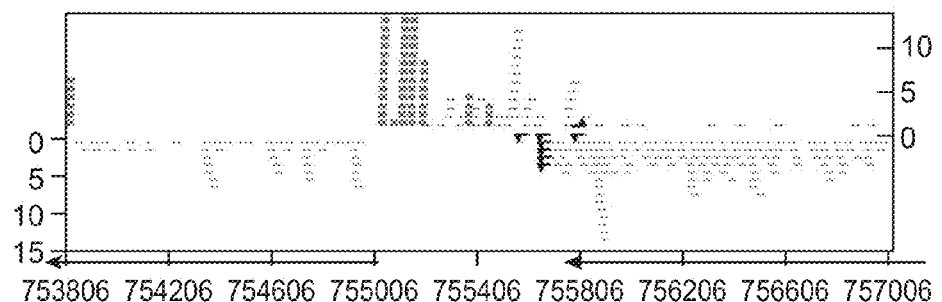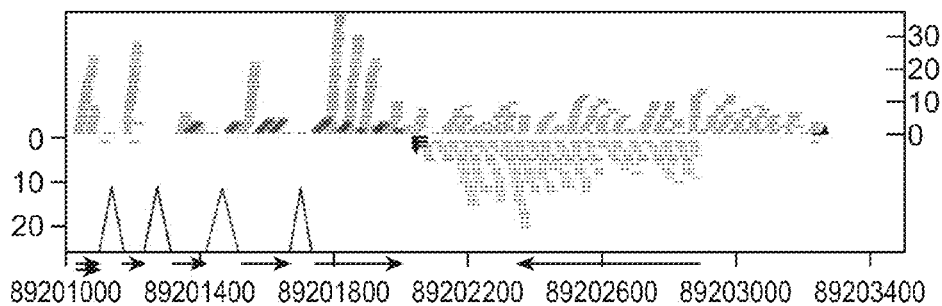
FIG. 10

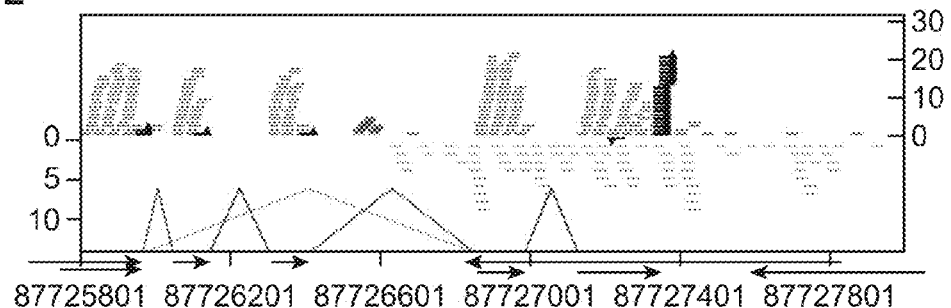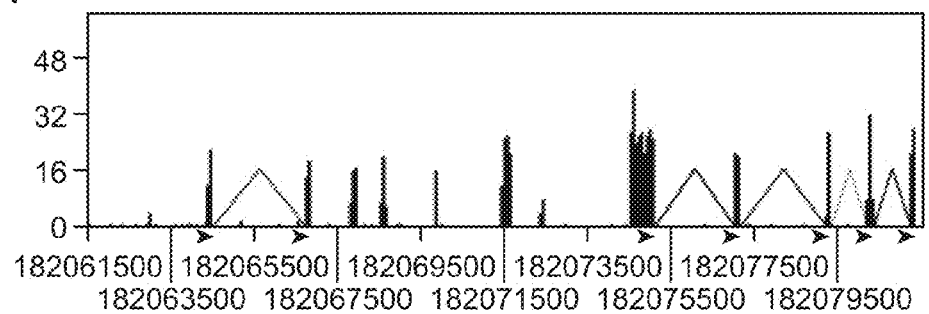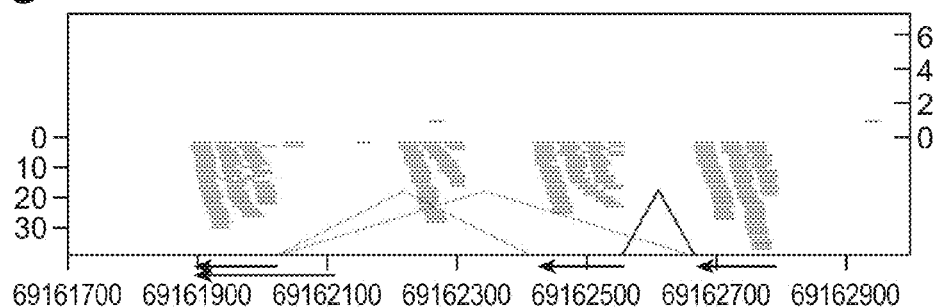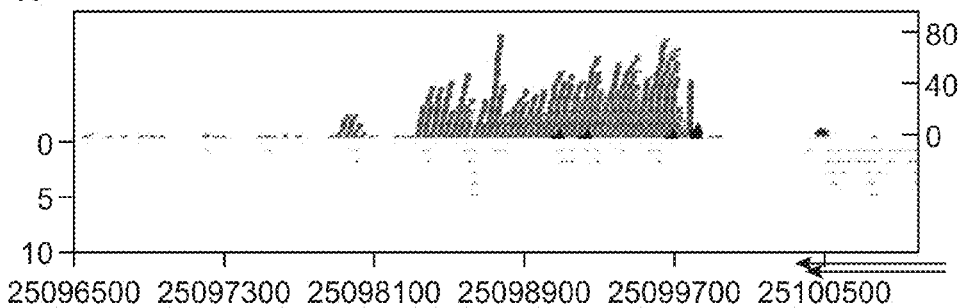
FIG. 10 (Cont.)

METHOD FOR DIFFERENTIATION OF POLYNUCLEOTIDE STRANDS

Cloning of single-stranded RNA and DNA molecules is much easier if they are transformed into double-stranded DNA. The invention relates to methods of preserving information about the direction of the original single-stranded molecules after being transformed into a double-stranded form.

Single-stranded RNA and DNA molecules play an important role in molecular biology. A number of viruses have single-stranded genomes. Most RNAs are present in single-stranded form. Recent studies have demonstrated an unexpected complexity of eukaryotic transcriptomes. A transcriptome is the set of all RNA transcripts produced in one or a population of cells. In addition to classical mRNAs (messenger ribonucleic acids) which cover approximately 1.5 percent of the genome in most higher eukaryotes, a large number of non-coding RNAs (ribonucleic acids) with widely varying expression levels have been identified. The biological functions of these novel transcripts are largely unknown and represent a new research area requiring high throughput transcriptome studies.

The polarity of the transcript is important for correct annotation of novel genes because it provides essential information about the possible function of a gene both on the RNA (structure and hybridization to other nucleic acid molecules) and the protein level. In addition, many genomic regions give rise to transcripts from both strands simultaneously. Antisense transcription is characteristic for eukaryotic genes and is thought to play an important regulatory role. Overlapping genes are common for compact genomes of prokaryotes and lower eukaryotes. Knowledge of transcript orientation helps to resolve the problem of colliding transcripts and to determine correctly gene expression levels in the presence of antisense transcription.

BACKGROUND OF THE INVENTION

From the art several methods are known that preserve directional information using distinguishable adapters for different ends of double-stranded DNA.

Adapters may be ligated directly to single-stranded RNA molecules.

Special composite primers may be used for first-strand cDNA synthesis: Herein the 5'-part of the primer provides a directional information, the 3'-part (oligo(dT)) or random nucleotides) is able to form a duplex with the RNA. Recently, first-strand cDNA synthesis was performed from a tagged random hexamer primer and second strand synthesis from a DNA-RNA template-switching-primer.

Special homopolymeric adapters may be synthesised at the 3'-end of DNA molecules by Terminal Nucleotide Transferase.

DNA-RNA template-switching is used to attach a specific adapter to 3'-end of the DNA copy of the original single-stranded RNA molecule.

The main disadvantage of the adaptor-based approach is that only the ends of the clones preserve directional information. The problems are:
  (i) strand-specific operations (directional immobilization on a solid phase; production of a single-stranded DNA for hybridization, etc.) should act on the adaptor sequence. For long clones the efficiency of such operations is normally low. For example, strand separation where one of the strands contains a biotin molecule at the 5'-end is getting complicated if the length of the duplex is higher than 1 kb.
  (ii) after fragmentation internal parts of the clones lose the directional information.

A special approach which is able to keep directional information in any part of the sequence was suggested recently: All cytidine residues in the RNA were converted to undines by bisulfite treatment prior to cDNA synthesis. The problem is that this approach is laborious and also leads to the loss of about 30% of uniquely matched sequencing reads because a part of the genome complexity is lost during the transformation from the four-bases into the three-bases code.

A lot of biologically important nucleic acids function in a single-stranded form where the polarity is extremely important. But for basic molecular cloning procedures single-stranded polynucleotides should be converted into double-stranded DNA molecules, because
  most of restriction enzymes work only on double-stranded DNA;
  ligation of double-stranded molecules is much simpler in comparison with the ligation of single-stranded molecules;
  the result of PCR is a double-stranded DNA.

At the moment most of the protocols keep directional information in the form of distinguishable adaptors on the ends of double-stranded molecules (FIG. 1B).

US 2007/0281863 discloses a method for characterizing the amounts of nucleic acids, including plus/minus determinations. To this end the mRNA is transcribed into double stranded cDNA and two different RNA promoters are integrated in both cDNA strands respectively. By using the different RNA promoters in the presence of allylamine-UTP nucleotides plus or minus RNA with modified allylamine-UTP nucleotides is generated. The modified allylamine-UTP nucleotides can be labeled with NHS-Cy3/5 and are then hybridized in different nucleic acid arrays.

The main disadvantage of this approach is that the RNA cannot be used for high-throughput complementary DNA sequencing (RNA-Seq). Direct cDNA sequencing (RNA-Seq) is a new tool for whole-transcriptome analysis. Second generation sequencing machines have increased sequencing throughput by about two orders of magnitude, making global transcriptome sequencing feasible. Since sequencing costs are constantly decreasing (contrary to those of microarrays) cDNA sequencing will capture a considerable portion of transcriptome analyses in the future.

The RNA-Seq procedure is simple, has a large dynamic range and high sensitivity, and can unequivocally identify splicing and RNA editing products as well as allele-specific transcripts. RNA-Seq provides a number of further advantages over other high throughput approaches like microarray hybridization, gene-specific and tiling arrays or SAGE-analyses. The depth of RNA-Seq analyses is flexible, providing a dynamic range typically an order of magnitude greater than one can achieve with hybridization arrays. The digital character of the RNA-Seq data permits to compare and pool results from different laboratories. No prior information about transcripts sequences is required, allowing detection of novel transcripts. It is possible to estimate the absolute level of gene expression and to study structure of transcripts.

However, the weakness of RNA-Seq was the inability to determine the polarity of RNA transcripts without laborious modification of the protocol. The method according to the invention solves this problem allowing the strand specific differentiation with an easy, robust and cheap procedure. The method is less susceptible and more robust compared to the method described in US 2007/0281863 because there is no need to transcribe the mRNA first in cDNA then inserting two different promoters in the cDNA and then using two different polymerases to transcribe the cDNA again in RNA including an additional step to label the marked RNA with NHS-Cy3/5.

Thus, the modified allylamine-UTP RNA according to US 2007/0281863 can only be used in hybridization arrays that are very expensive, less sensitive and cannot detect novel transcripts. Additionally, the method is laborious including the integration of promoters and different polymerases and works with RNA as an end product, which is very susceptible to degradation because of abundant RNases and can only be used in expensive hybridization arrays that are less sensitive then e.g. RNA-Seq.

Further disadvantages include that many basic molecular cloning procedures are performed on double stranded cDNA, which are necessary for many subsequent analyzing methods. The method according to US 2007/0281863 generates a double stranded cDNA with two promoters as an intermediate product. However, these intermediate cDNAs are not preferred for cloning procedures, As we already explained above the main disadvantage of adaptor-based approaches is that only the ends of the clones preserve directional information. The integration of promoters in the cDNA is basically the same procedure. During cloning procedures the promoters can be changed, damaged etc., especially because most cloning procedures modify the ends of the cDNA. The subsequent strand specific transcription of the cDNA with promoter specific polymerases is thus not very robust and the strand specific information can be lost during molecular cloning procedures. Taking into account the susceptibility of RNA to degradation, the method according to the instant application is more functional, i.e. the RNA is transcribed directly into cDNA and the strand specific information is already integrated in this step. Furthermore, the inventive method is much more robust, e.g. the cDNA already contains the strand specific information along the whole length of the transcript and no molecular cloning procedures can compromise this information. Consequently, the inventive method is convenient, reliable and highly reproducible.

WO 97/12061 discloses a method for characterizing nucleic acid molecules, comprising synthesizing DNA with a nucleic acid matrix, primers, polymerase, four canonical deoxynucleotides and at least one non-canonical deoxynucleotide. The DNA is then contacted with N-glycosylase and the abasic sites are treated in a way to leading to breakage of the phosphodiester backbone. The resulting DNA fragments are separated according to their size.

This method characterizes DNA according to their size by using non-canonical deoxynucleotide to label one synthesized DNA strand, but the method is not able to preserve the information about the direction of the original single-stranded molecules after being transformed into a double-stranded form.

DESCRIPTION OF THE INVENTION

The objective of the present invention is to provide a method for keeping the directional information in double-stranded DNA. Surprisingly, it was found that this objective can be reached by the inventive method as disclosed by the description, the figures and the examples. A polynucleotide strand is converted into a hybrid double-stranded DNA. One particular strand of this hybrid double-stranded DNA should be synthesised using at least one modified nucleotide. Thus, this particular strand would contain modified nucleotides along the whole length of the strand. The density of directional markers would not depend on the length of hybrid double-stranded DNA. Any internal fragment of the hybrid would have directional information. It was found that such hybrid double-stranded DNA may be easily generated in a number of molecular biology tasks and may be used for molecular cloning, library preparation and strand separation. If necessary, one of the strands (modified or non-modified) may be easily degraded or separated from the other strand. Also some modifications might prevent the strand containing modified nucleotides from participation in downstream applications.

The directional library construction method and the method of synthesis of single-stranded DNA according to the invention are easy to perform, inexpensive and highly reliable and thus overcome the shortcomings of the state of the art approaches.

The inventive method for preserving information about the direction of single-stranded nucleic acid molecules during molecular cloning operations with double-stranded DNA is provided. One of the strands of the double-stranded DNA is synthesized by using the other strand as a matrix and contains at least one modified dNTP. Thus, one strand of double-stranded DNA would contain unmodified nucleotides and the other strand at least one modified nucleotide along the whole length (FIG. 1C).

The new method of keeping of direction of polynucleotides is fully compatible with methods known from the art. Double-stranded DNA molecules may have simultaneously distinguishable primers and distinguishable strands (FIG. 1D). FIG. 2A shows how molecules with distinguishable strands may be converted into molecules with distinguishable primers. In an opposite operation the conversion of molecules with distinguishable primers into molecules with distinguishable strands is shown in FIG. 2B.

The main advantages compared to the adaptor-based method are:
  (i) the density of modified nucleotides (directional markers) does not depend on the length of the double-stranded molecule. This is important for strand separation or strand-specific digestion of long DNA molecules.
  (ii) any internal fragment of the clone carries directional information. After fragmentation internal parts of the clones do not lose the directional information.

Two examples demonstrate the convenience of the inventive method for differentiation of polynucleotide strands.

Figures 1, 2A:
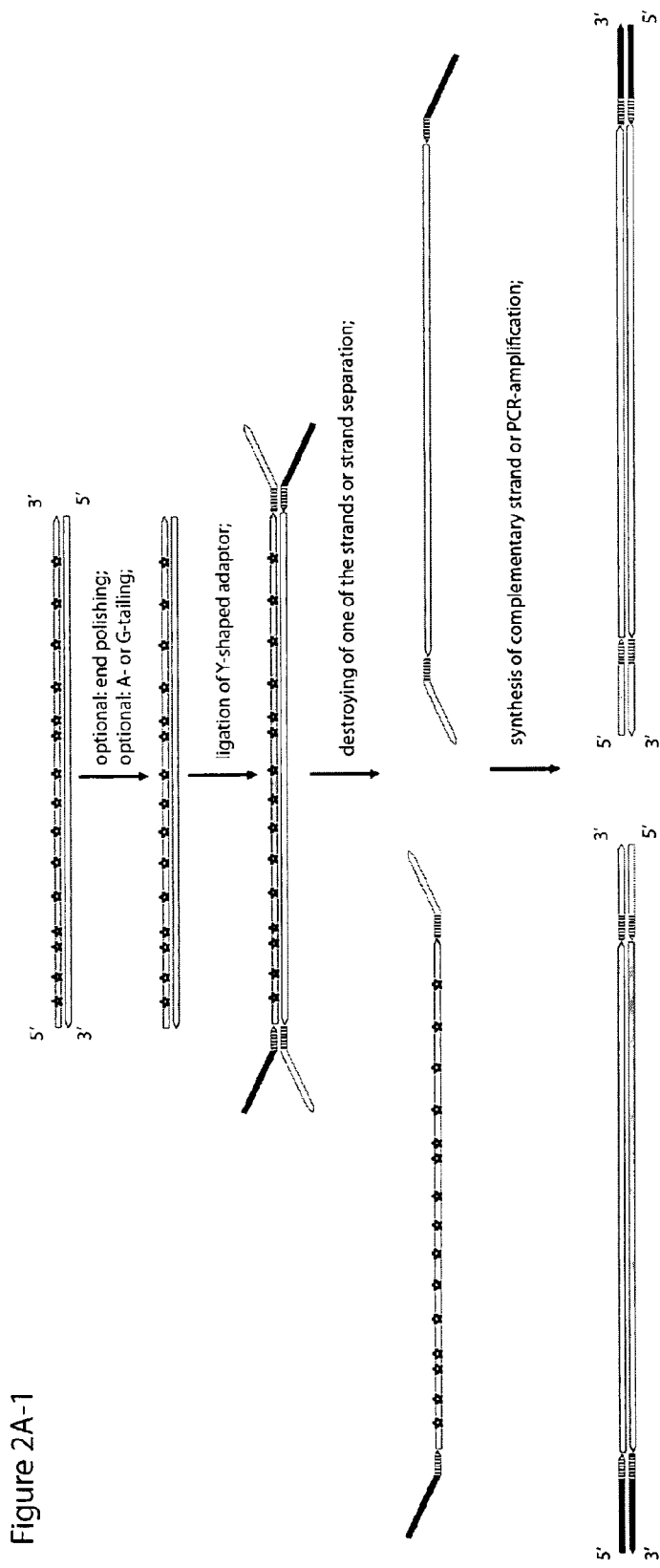
Figures 2, 2A:
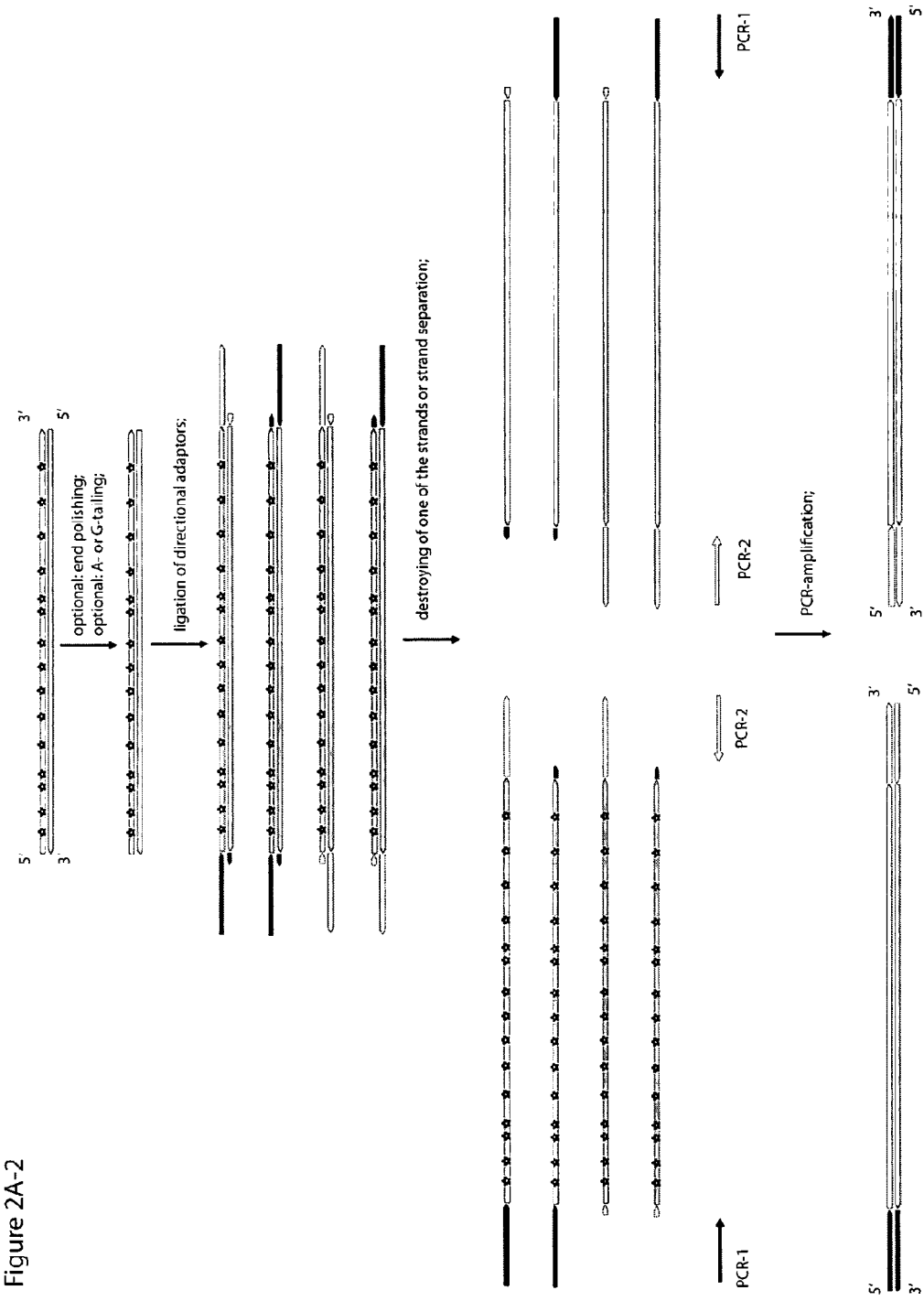
Figures 2, 2A, 3:
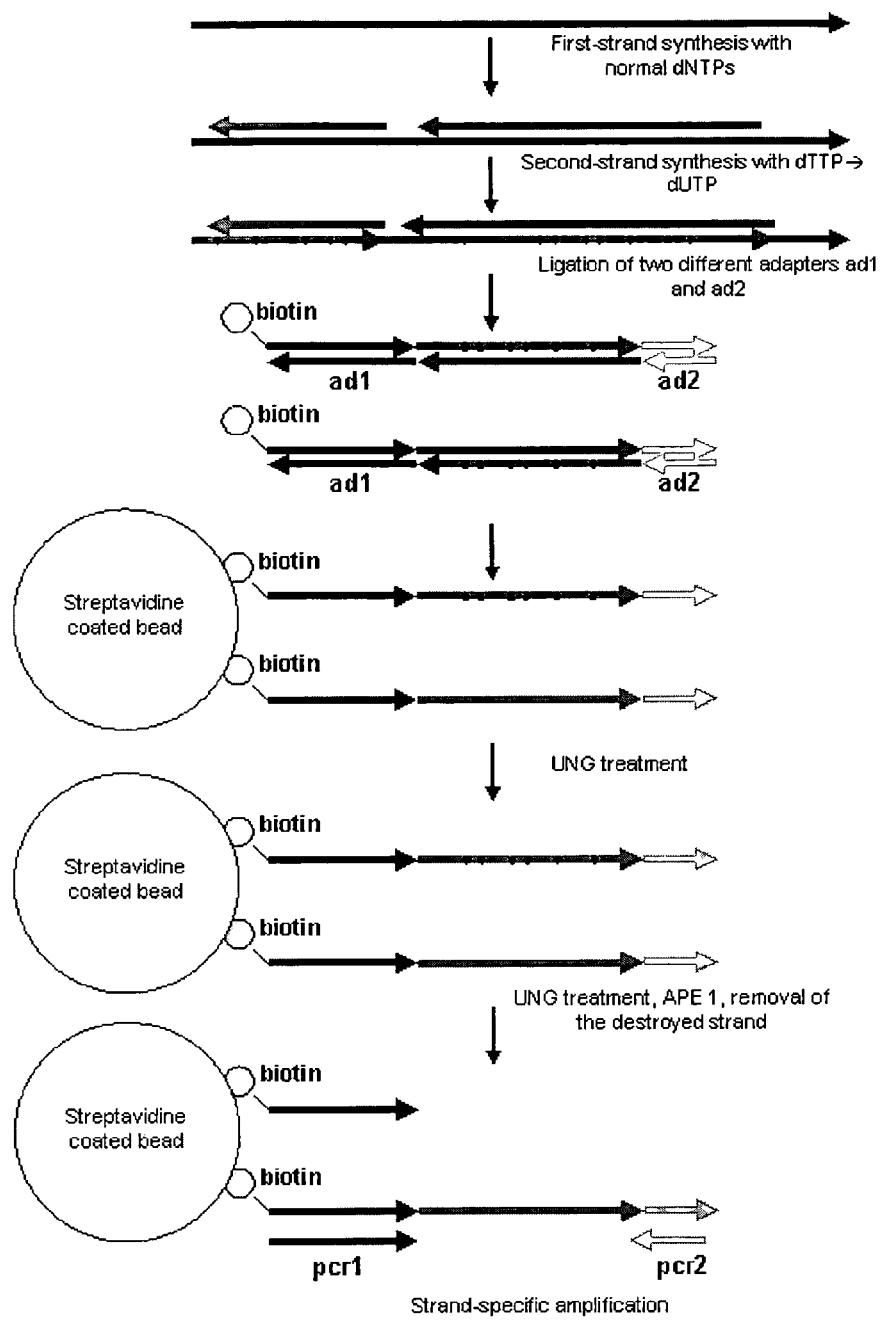

The method of synthesis of a single-stranded DNA is described in FIG. 3.

There is a number of methods of synthesis of single-stranded DNA relying on the difference between flanked adaptors:
  asymmetric PCR may be performed with the different amounts of PCR primers;
  the 5' end of one of the strands may contain thionucleotides which protect this strand from 5' to 3' exonucleases;
  protective thionucleotides may be introduced into the 3'-end part of only one strand to protect it from 3' to 5' exonucleases;
  the 5'-part of one of the strands may bear biotin for attachment of this strand to streptavidine-coated solid particles.

The problem is that all these methods proved to be unstable and show low efficiency for molecules larger than 1 kb.

FIG. 3 shows two possible ways for generating single-stranded DNA using the inventive method for differentiation of polynucleotide strands.

In a first embodiment of the present invention (FIG. 3A) one strand of PCR product is substituted by a strand where dTTPs are substituted by dUTPs. After UNG treatment and APE 1 digestion (or alkalic hydrolisis) this strand is converted into a number of short single-stranded fragments which may be easily separated from the long unmodified strand by electrophoresis, anion-exchange chromatography, silica-based purification or gel-filtration.

In a second embodiment of the present invention (FIG. 3B) one strand of the PCR product is substituted by a strand where a significant percentage of the dTTPs is substituted by biotin-associated dUTPs, respectively biotin-associated dTTPs. The concentration of biotin in a modified strand does not depend on the length of the double-stranded DNA, so the efficiency of the purification on streptavidine-coated particles should not depend on the length of the fragment.

The key steps of the method according to the invention include the generation of a cDNA strand including at least one modified nucleotide that in the course of the method is recognized by a selection factor which allows for selection of the strand containing the at least one modified nucleotide from the strand containing the corresponding unmodified nucleotide or nucleotides.

The key steps of the inventive method are to be read in the following order:
I) Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on said polynucleotides; and
III) Performing strand-specific selection by using a selection factor for selecting strands containing the at least one modified nucleotide from strands containing the corresponding unmodified nucleotide.

The key steps of the inventive method can also be read in the following order:
I) Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific differentiation;
II) Performing specific strand synthesis on said polynucleotides; and
III) Performing strand-specific differentiation by using a selection factor for differentiating strands containing the at least one modified nucleotide from strands containing the corresponding unmodified nucleotide.

The term strand specific differentiation refers to the ability to differentiate in the double stranded form between the template and the synthesized matching strand.

The term specific strand synthesis refers to synthesis of the matching strand containing the at least one modified nucleotide from the template.

Another embodiment of the present invention relates to single-stranded RNA. Thus, if the polynucleotide template is a single-stranded RNA a second cDNA strand has to be synthesized. For this purpose the at least one modified dNTP has to be removed from the solution and has to be replaced by the corresponding unmodified dNTP or dNTPs or analogues thereof. By the use of all four unmodified dNTPs a second cDNA strand is generated.

In this case the key steps according to the inventive method read as follows:
I) Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on said polynucleotides;
III) Performing second-strand synthesis with all four unmodified dNTPs or analogues thereof after removing the at least one modified dNTP; and
IV) Performing strand-specific selection by using a selection factor for selecting strands containing the at least one modified nucleotide from strands containing the corresponding unmodified nucleotide.

As said before, if the polynucleotide templates are single-stranded RNA a second-strand cDNA has to be synthesized after the exchange of the at least one modified dNTP by the corresponding unmodified dNTP or dNTPs. If this double-stranded cDNA shall undergo cloning it will be advantageous to perform one or more of the modifications for the molecular cloning operation as described before. By combining these conditions the key steps of the invention read as follows:
I) Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on said polynucleotides;
III) Performing second-strand synthesis with all four unmodified dNTPs or analogues thereof after removing the at least one modified dNTP;
III) Performing one or more molecular cloning operations on the double-stranded DNA, wherein the molecular cloning operations are selected from shearing, restriction, digestion, end-polishing, A-tailing, G-tailing and adaptor ligation; and
V) Performing strand-specific selection by using a selection factor for selecting strands containing the at least one modified nucleotide from strands containing the corresponding unmodified nucleotide.

The initially provided polynucleotide templates may be a RNA such as mRNA, tRNA, rRNA, hnRNA, snRNA, snoRNA, scaRNA, asRNA, micro RNA, siRNA, short transcripts, single-strand oligonucleotides, single-strand polynucleotides, synthetic polynucleotides and semisynthetic polynucleotides as well as physiological or externally induced modifications thereof, wherein mRNA is preferred.

mRNAs are protein-coding RNA. tRNAs are transfer RNAs responsible for providing correct amino acids in peptide (protein) synthesis in ribosomes. rRNAs are ribosomal RNAs, being a constitutive element of ribosomes. hnRNAs (heterogeneous nuclear RNA) is a precursor mRNA in the nucleus of eukaryotic cells. It is often named also pre-mRNA or precursor mRNA. snRNA (small nuclear RNA) is responsible in the eukaryotic nucleus for the processing of hnRNAs (spliceosomes). snoRNA (small nucleolar RNA) occurs in the nucleolus of eukaryotic cells. scaRNA (small Cajal body-specific RNA) is strongly related to snoRNA and occurs in Cajal bodies. asRNA (antisense RNA) plays an important role in regulating gene expression. microRNAs are involved in the regulation of cellular processes such as apoptosis and cell death. siRNA (small interfering RNA) is processed from cellular RNA into fragments with a length of ca. 22 base pairs by the enzyme Dicer and integrated into the enzyme complex RISC (RNA-induced silencing complex). RISC can thus regulate the expression of DNA segments or RNAs by switching off the respective coding region through analogous base pairing (silencing). This method by also used in gene therapeutic approaches. Retroviruses use RNA as the carrier of their genetic information.

Short transcripts refer to small RNA fragments with up to 20-40 base pairs.

Alternatively, the polynucleotide templates used within the inventive methods may be a DNA such as siDNA, DNA copies from retroviral or hepadnaviral RNA, single-stranded DNA, synthetic polynucleotides and semisynthetic polynucleotides as well as physiological or externally induced modifications thereof, wherein single-stranded DNA is preferred.

It shall be pointed out that in this invention the term single-stranded DNA can also refer to the first-strand cDNA derived from a RNA as templates.

siDNA (small interfering DNA) is the corresponding DNA of siRNAs and mainly fulfils the same tasks in the cell. Single-stranded DNA is a single-stranded type of satellite DNA, occurring among others in certain soil-dwelling bacteria species.

According to the invention also double-stranded DNA can be the polynucleotide templates. Specific primers and optionally adjuvants are needed to allow the generation of a cDNA strand against a particular strand of the double-stranded DNA (see below and FIG. 2B). Herein, the double-stranded DNA is destabilized in the region of hybridization of said specific primer for allowing annealing of the specific primer. Such a destabilization can be achieved for example by Uracil-N-Glycosylase digestion of deoxyuridines.

In a specific embodiment the double-stranded DNA templates are PCR products.

Sources for RNAs and DNAs can be eukaryotes (animals including humans and other mammals, plants, fungi), prokaryotes (bacteria, archaea), viruses, synthetic or semi-synthetic constructs wherein these constructs or semisynthetic constructs may mirror at least partially a naturally occurring nucleic acids or may have a widely artificial sequence.

Said RNAs and DNAs can be isolated by well-known methods (Molecular Cloning: A Laboratory Manual, Third Edition. J. Sambrook, D. Russell).

The term classic dNTPS, respectively unmodified dNTPS refers to dATP (deoxyadenosine triphosphate), dCTP (deoxycytidine triphosphate), dGTP (deoxyguanosine triphosphate) and dTTP (deoxythymidine triphosphate). These four dNTPs (deoxynucleoside triphosphates) are usually used in nature for the generation of DNA strands.

It shall be pointed out that the plural form classic dNTPs refers to the total of dATP, dCTP, dGTP and dTTP. A referral in a quantifying sense to one or more of these classic dNTPs is not intended.

The term analogues of dNTPs, respectively dNTPs and analogues thereof refers to any molecule suitable for replacing a dNTP in presence and behavioural characteristics in a respective polynucleotide-containing solution and particularly in its matching characteristics to be able to undergo a base pair matching identical or similar to the classic dNTP it replaces. In particular, such analogues of dNTPs should be able to build the same or similar selective hydrogen bonds that allow for a selective pairing of base pairs (2 hydrogen bonds between NT, T/A, A/U or U/A, and 3 hydrogen bonds between G/C and C/G), thus allowing for a correct translation of a polynucleotide sequence into its antisense sequence. Furthermore, it should be sterically similar to its corresponding classic dNTP so that it allows integration into the base pair sequence. Not only the nucleotide can be varied in such an analogue, but also the saccharide moiety (usually a ribose or deoxyribose) or the phosphate backbone. For example, the phosphate backbone may be partially or entirely substituted by a sulphonated backbone and/or by a phosphonate backbone. Also combinations of such variations are subsumed under this term.

Moreover the analogues of the dNTPs cannot be used for stand specific selection or strand differentiation. Thus the analogues of the dNTPs do not react under the conditions which are used for the modified dNTPs such as degradation (e.g. dUTP, heat), differentiation by e.g. electrophoretic methods, adsorption or binding to suitable counterparts such as biotin—avidin. Thus the analogues of the dNTPs are used as substitutes for the classic or canonical dNTPs and not as substitutes for the modified dNTPs.

The quantitative term sufficient amount herein refers to any amount, respectively concentration of an agent which allows for a qualitative and quantitative implementation of the method according to the invention in respect of the expected amounts which shall be needed for this purpose. Usually, the respective agents, in particular dNTPs, are added in exceeding amounts in order to ensure that all possible copies can be effected qualitatively and quantitatively.

The term template refers in molecular biology to a DNA or RNA strand which sets the base pair sequence to which a corresponding strand with an antisense sequence shall by polymerized. In a broader sense it may also refer to a RNA encoding a sequence for translation of this sequence into an amino acid sequence such as a peptide or a protein in ribosomes. The term templates in plural refers to the total sum of polynucleotides provided, each single template representing a single polynucleotide. Templates also refers to the originally provided sum of polynucloetid strands. to A referral in a quantifying sense to one or more of these templates is not intended.

The term template refers also to the original single stranded polynucleotide strand, where the preservation of information about the direction is desired after being transformed into a double-stranded form. If the inventive method is applied to double stranded polynucleotides (e.g. DNA/RNA, DNA/DNA with distinguishable adapters), in this case the template can be freely chosen from both strands, depending for which strand the preservation of information about the direction is desired.

The term matching strand refers to the complementary strand to the template.

The term first-strand synthesis refers to the synthesis of the first strands using the templates as matrix for synthesizing the complementary strands. The nucleotide sequence of the first strand corresponds to the sequence of the matching strand.

The term second-strand synthesis refers to the synthesis of the second strands that uses the first strands as matrix for synthesizing the complementary strands, i.e. the second strands. The nucleotide sequence of the second strand corresponds to the sequence of the template.

As used herein the term "matrix" or "matrices" refers to any polynucleotides which can serve as starting material for polymerase-reactions.

As used herein the term "at least one nucleotide" or "at least one modified nucleotide" is not meant as a referral in a quantifying sense to one or more nucleotides but refers to a species of modified dNTPs. Thus, this term refers to a plurality of dNTP molecules of the same kind. Thus using "one" modified nucleotide does not mean that a single modified nucleotide is used. Using "one" modified nucleotide means that one kind or one sort of nucleotides are used which are modified such as modified dATP or modified dCTP or modified dGTP or modified dTTP.

The term "replaced by a corresponding modified dNTP" refers to a substitution of one of the classic or canonical dNTP species in the reaction mixture used for strand synthesis by a modified dNTP species able to fulfil the same biological function. This means that the substitution is not performed on the completed strand after strand synthesis. The term "same biological function" refers to modified dNTPs able to preferably build the same or similar selective hydrogen bonds that allow for a selective pairing of base pairs (2 hydrogen bonds between NT, T/A, A/U or U/A, and 3 hydrogen bonds between G/C and C/G). Furthermore, it should preferably be sterically similar to its corresponding classic dNTP so that it allows integration into the base pair sequence. Not only the nucleotide can be varied in such a modified dNTP, but also the saccharide moiety (usually a ribose or deoxyribose) or the phosphate backbone.

The term cDNA stands for complementary deoxyribonucleic acid. It refers to a DNA which is generated as a copy of a RNA (usually by means of Reverse Transcriptase) or from a single DNA strand (usually by means of a DNA polymerase). Subsequently, a second cDNA strand may be generated by using the first cDNA strand as a matrix (usually by means of a DNA polymerase).

Enzymes with reverse transcriptase (RNA-dependent DNA polymerase) activity are able to transcribe a RNA sequence into a corresponding cDNA sequence. This group of enzymes includes among others HIV-1 reverse transcriptase from human immunodeficiency virus type 1 (PDB 1HMV), M-MLV reverse transcriptase from the Moloney murine leukemia virus, AMV reverse transcriptase from avian myeloblastosis virus and telomerase reverse transcriptase fulfilling a role in the maintenance of telomeres of eukaryotic chromosomes as well as commercially available forms such as "M-MLV reverse transcriptase RNase H Minus", "SuperScript® II", "SuperScript® III" or Tth polymerase. Among this group M-MLV reverse transcriptase RNase H Minus, SuperScript® II and SuperScript® III polymerases are preferred.

The terms primers and random primers refer to oligonucleotides which shall serve as starting point for DNA-replicating enzymes such as DNA polymerases. They can consist of a few base pairs, but in selected cases can reach up to 2.000 base pairs. Preferred are 5 to 50 base pairs. DNA polymerases need a hydroxy group for starting transcription. This hydroxy group is provided by the primer with its 3' hydroxy end. Often, the DNA sequence to be investigated is known. Hence suitable primers can be synthesized precisely according to the antisense sequence of aforesaid polynucleotide sequence. If this polynucleotide sequence is not or only incompletely known so-called random primers can be used. In such a method a large number of primers with a random base pair sequence are provided. One or more of these random primers statistically anneal to the polynucleotide sequence that shall be transcribed. Thus corresponding transcripts of different length can be obtained, depending where the random primer anneals to the polynucleotide sequence of interest. Alternatively, also composite primers with a random 3' part can be used. A further variation corresponding to the inventive method is the use of primers which are complementary to a homo-oligomeric tail synthesized by terminal transferase on the polynucleotide which serves as a matrix.

If the polynucleotide templates are RNA with a polyA tail it is preferred that said primers are oligo(dT), oligo(dU) or oligo(U) primers or composite primers with oligo(dT), oligo (dU) or oligo(U) region on 3' part. Alternatively, specific primers complementary to said single-stranded RNA templates can be used.

If double-stranded DNA templates are used it is likewise possible to mark one particular strand of the double-stranded DNA with at least one modified nucleotide. Herein specific primers complementary to a particular strand of said double-stranded DNA can be used. In this case RecA protein may facilitate the hybridization of said primers to the double-stranded DNA templates. Specific primers may appear as a result of introducing a nick in a particular strand of said double-stranded DNA templates. Such nicks can for example result by the use of nicking endonuclease. Alternatively, such nicks may result from the digestion of the at least one modified nucleotide in a particular strand of said double-stranded DNA templates.

In a specific embodiment the double-stranded DNA templates are PCR products. In this case, the recognition site of a nicking exonuclease or at least one modified nucleotide is located in one of the PCR primers. Herein it is preferred that said modified nucleotide is deoxyuridine.

If double-stranded DNA templates are used it is preferred that said polymerase is a DNA-dependent DNA polymerase with 5' to 3' exonuclease activity and said strand-synthesis on such double-stranded DNA templates are effected by means of a nick-translation.

In analogy, the polynucleotide templates may be also a DNA::RNA hybrid. Hybrid herein means that a DNA strand is matching with a RNA strand having a corresponding antisense sequence. For example, but not limiting, it is possible that such a DNA::RNA hybrid is the product of a first-strand synthesis with unmodified nucleotides generated on single-strand RNA as templates. For generating a cDNA of the DNA strand specific primers complementary to a particular DNA region of said double-stranded DNA::RNA hybrid have to be used. It is preferred that said primers are complementary to a homo-oligomeric tail synthesized by terminal transferase. In another preferred embodiment this specific primer is a template-switch-primer. Such template-switch primers bind to the extra random nucleotides attached to the 3' end of the newly synthesized cDNA strand by using SuperScript® II enzyme (Invitrogen). This allows for full-length reverse transcription of the RNA strand. If the cDNA strand shall be generated against the RNA strand of the DNA::RNA hybrid said polymerase is DNA-dependent DNA polymerase with 5' to 3' exonuclease activity.

If the cDNA strand shall be generated against the DNA strand of the DNA::RNA hybrid the specific primers may appear as a result of introducing a nick into the RNA strand of said DNA::RNA hybrid. Such a nick may be set by using the RNA-specific enzyme RNase H. In a preferred embodiment RNase H, DNA polymerase I and *E. coli* ligase are used simultaneously. DNA ligases are enzymes able to ligate DNA strands by building an ester bond between the phosphate residue and the saccharide deoxyribose in the backbone of the DNA strands.

For second-strand cDNA synthesis using the first strand cDNA as a matrix an enzyme with DNA polymerase activity is needed. Also if the original polynucleotide is a single-stranded DNA and only one cDNA strand is generated such an enzyme with DNA polymerase activity is needed. DNA-dependent DNA polymerases are usually enzymes which generate a DNA copy strand from a DNA matrix. This group includes DNA polymerase I, II, III holoenzyme and IV, Taq polymerase, Tth polymerase, Pfu polymerase, wherein DNA polymerase I and Taq polymerase are preferred. This enzyme with polymerase activity does not have to be the same as used optionally for amplifying the remaining intact cDNA.

If the cDNA strand shall be generated against the RNA strand of the DNA::RNA hybrid the procedure is similar to that for generating a cDNA strand against one strand of a single-stranded RNA.

The term modified dNTP refers to any molecule suitable for substituting exactly one corresponding classic dNTP in presence and behavioural characteristics in a respective polynucleotide-containing solution and particularly in its matching characteristics to be able to undergo a base pair matching identical or similar to the classic dNTP it replaces. Additionally, this modified dNTP must be suitable either for a specific degradation in which selectively this modified dNTP is degraded by a suitable degrading agent, thus rendering the DNA strand containing at least one of this degraded dNTP essentially unfit for amplification and/or hybridization, or it must render the DNA strand containing this modified dNTP eligible for specific removal of this DNA strand from the solution, or at least allowing a local and thus functional separation of polynucleotide strands. Such a removal respectively separation can be achieved by molecules or particles binding selectively to such exchange dNTPs, thus selectively only to one polynucleotide strand. Removal can occur by purification, adsorption to suitable structures or surfaces, binding to suitable selective structures such as antibodies, by selective degradation through certain chemicals, heat or radiation, or by centrifugation, magnetic or electrophoretic methods, isoelectric focusing. Also any kind of immobilization can be perceived.

The term canonical is used to refer to the four common nucleic acid bases adenine, cytosine, guanine and thymine that are commonly found in DNA or to the respective deoxyribonucleosides, deoxyribonucleotides or 2'-deoxyribonucleoside-5'-triphosphates that contain a canonical base. The term "non-canonical" is used to refer to nucleic acid bases in DNA other than the four canonical bases, or to the respective deoxyrinonucleosides, deoxyribonucleotides, or 2'-deoxyribonucleoside-5'-triphosphates that contain a non-canonical base. Although uracil is a common nucleic acid base in RNA, uracil is a non-canonical base in DNA. "Non canonical bases" are found in nucleic acids as a result of incorporation of non-canonical nucleotides or as a result of modification of existing bases (canonical or non-canonical).

Different purification methods may be used for removal of modified and unmodified dNTPs from the solution: electrophoretic separation, salt-alcohol precipitation, anion-exchange chromatography, silica purification, gel filtration. Purification on silica and gel-filtration are preferred.

Degradation respectively degradable herein means that a deoxynucleotide is specifically modified by addition of at least one enzymatic, chemical, heat, radiation (X-ray, UV, microwave) or optical methods such as lasers or combinations thereof in such a way that the resulting deoxynucleotide does not serve anymore for hybridization, cloning or as a suitable matrix in an amplification system such as PCR.

Analogously, the plural form modified dNTPs refers to the total of the respective modified dNTPs. A referral in a quantifying sense to one or more of these modified dNTPs is not intended.

The term at least one modified dNTP refers to the option that not only one dNTP is exchanged. According to the invention either one dNTP such as dATP, dCTP, dGTP or dTTP, or two dNTPs can be exchanged in the combinations dATP+dCTP, dATP+dGTP, dATP+dTTP, dCTP+dGTP, dCTP+dTTP or dGTP+dTTP, or three dNTPs can be exchanged in the combinations dATP+dCTP+dGTP, dATP+dCTP+dTTP, dATP+dGTP+dTTP or dCTP+dGTP+dTTP, or all four dNTPs are exchanged in the combination dATP+dCTP+dGTP+dTTP. It is understood that also analogues of these dNTPs as defined before shall be subsumed under the respective dNTPs. Also possible quantitative combinations thereof shall be subsumed under this combinational scheme.

The term selection, selecting or strand specific selection refers to selecting in ds (double stranded) polynucleotides the strand with at least one modified nucleotide to distinguish the template from the matching strand. The selected strand with the at least one modified nucleotide in ds (double stranded) polynucleotides can be selectively removed or specifically destroyed, while the strand without modified nucleotide is not impaired preferably throughout its whole length. The removed or destroyed or destroyable strand with the modified nucleotide can be used separately. If the strand with the modified nucleotide is not removed and/or destroyed, it can remain in the same solution with the matching strand. The modified nucleotide in the strand prevents full-length amplification of the strand.

There are several principles by which a selection factor can be used to select between a strand marked with at least one modified nucleotide and a strand with the corresponding unmodified nucleotide or nucleotides. For example, the at least one modified nucleotide has a chemically active group that can be modified after strand-specific synthesis. Another possibility is that the at least one nucleotide carries an affinity group and the selection factor binds selectively to this affinity group. Such am affinity group may for example be recognized by an antibody. A further possibility is that the at least one modified nucleotide carries a group which allows for selective recognition and binding or attachment by another agent which then enables selective removal of the such recognized strand. A further selective factor may be a different sensitivity to specific nucleases. Also the incorporation of ribonucleotides (NTPs) instead of deoxyribonucleotides (dNTPs) is suitable for enabling selection between two strands.

The at least one modified nucleotide may display a different sensitivity to a nuclease, in comparison with the corresponding unmodified nucleotide or nucleotides. Thus such nuclease degrades specifically the at least one modified nucleotide while the unmodified nucleotides are not or only insignificantly affected by such nuclease action. Alternatively, such nuclease degrades specifically the unmodified nucleotides. In both cases the strand containing the such degraded nucleotide or nucleotides has become unfit for amplification or hybridization. Thus both strands can be differentiated, and only one particular strand may be further used.

In a preferred embodiment the selection of strands of polynucleotides is carried out with the modified dNTP being dUTP (deoxyuridine triphosphate). Herein the modified dNTP is dUTP (deoxyuridine triphosphate) as a substitute for dTTP. dUTP displays the same matching characteristics as dTTP, i.e. it is able to match with an opposed adenosine, but not with opposed guanosines, cytosines, thymidines or uridines. dUTP can be specifically degraded by the nuclease Uracil-N-Glycosylase (UNG). UNG is neutral towards dTTP and the other dNTPs or analogues thereof. This enzyme degrades uracil specifically by cleaving the N-glycosylic bond resulting in an abasic site. The such degraded DNA strand is unfit for undergoing appropriate amplification. At temperatures of over 50° C. in slightly alkali conditions nicks occur in the DNA strand at the abasic positions. Additionally, Phusion DNA polymerase preferentially used for amplification (see below) is strongly suppressed by deoxyuridine-containing matrices (Hogrefe, H. H., Hansen, C. J., Scott, B.

R. and Nielsen K. B. 2002. Archaeal dUTPase enhances PCR amplifications with archaeal DNA polymerases by preventing dUTP incorporation. Proc Natl Acad Sci USA 99: 596-601). Consequently, only the DNA strand that does not contain dUTP can be amplified properly.

The combination of dUTP as exchange dNTP and UNG as the degrading agent of the exchange dNTP is a preferred embodiment. It is also preferred to replace only dTTP.

In another preferred embodiment the at least one modified nucleotide is thio modified and said nuclease is an exonuclease that degrades thio bonds with low efficiency. Such exonucleases sensitive to thio bonds can be lambda-exonuclease, Exo III nuclease, T4 polymerase and T7 exonuclease.

Other preferred dNTP-specific degradation systems include the use of specific biotinylated dNTPs. Herein NHS esters of biotin are reacted with free amino groups of the respective nucleotide. These biotinylated nucleotides can be recognized by polymerase enzymes as eligible for integration into the actually formed strand. The matching properties to their counter nucleotide on the other strand are comparable. The biotinylated strand might be removed using streptavidin- or avidin-coated magnetic particles. Such specifically attached magnetic particles can be removed by applying a suitable magnetic field.

In another preferred embodiment the at least one modified polynucleotide is an aminoallyl nucleotide (5-(3-aminoallyl)-nucleotide, aa-dNTP). Herein the nucleotide has an aminoallyl group attached to carbon 5 of the pyrimidine ring of uracil and cytosine. This aminoallyl group reacts with dyes from the cyanine series such as HiLyte Fluor® or Alexa Fluor® dyes that also been modified to be amine-reactive. As these dyes use to react also with standard buffer mediums a carbonate buffer is typically used. Herein it is preferred that the modified nucleotide is aminoallyl-dUTP.

In a further preferred embodiment the modified nucleotide can be selectively recognized by an antibody. The antibody binds specifically to this modified nucleotide and the strands are selected by binding or immobilizing said antibody. It is further preferred that such antibody recognizes specifically the modified nucleotide 5-bromodeoxyuridine. It is also further preferred that such antibody or antibodies recognize specifically at least one modified nucleotide that has been modified by biotinylation.

If the strand carrying at least one modified nucleotide which carries a group which interacts which an affinity factor it is preferred that such strand is immobilized on a solid phase.

In a further preferred embodiment the at least one modified nucleotide is a ribonucleotide. Then it is preferred that said polymerase is a DNA polymerase displaying enhanced ability to incorporate modified substrates such as ribonucleotides (for example, Therminator™ II DNA Polymerase). The such incorporated at least one ribonucleotide is then specifically degraded by a specific nuclease, in this case a RNase.

If at least one classic dNTP is replaced by the corresponding modified dNTP(s) to generate a modified DNA strand the ratio of the at least one modified dNTP shall amount to at least 5% of the corresponding classic dNTP in the solution. Preferred are 20% ratio, more preferred 30%, more preferred 40%, more preferred 50%, more preferred 60%, more preferred 70%, more preferred 80% and particularly preferred more then 90%. Theoretically, only one degraded nucleotide is enough to render the degraded strand unfit for appropriate amplification. This requires that the DNA is long enough that at least one modified dNTP is integrated into the DNA strand. This is a matter of probability (when an even distribution of all four nucleotides is ideally assumed for the original polynucleotides) according to the distribution of the corresponding classic dNTPs and exchange dNTPs. With a length of at least 60 base pairs the probability is close to nil that not at least one modified dNTP has to be integrated into the second-strand cDNA. In order to ensure that also cDNAs with a length less than 60 base pairs always include at least one degradable nucleotide it is preferred that a sufficiently large percentage of the respective nucleoside triphosphate is modified.

If an amplification step is carried out in any of the embodiments of this invention an enzyme with polymerase activity is needed which is able to use the selected cDNA strand as a matrix. In theory, any such enzyme with polymerase activity is suitable for this step. However, those enzymes that are used in conventional PCR protocols are preferred. They should grant a high reliability and a high throughput under conventional PCR conditions.

To preserve information about the direction of the strand selected from a polynucleotide duplex for the further amplification., it is essential to mark differently the 5' and 3' ends of the said selected strand. This way the polarity of the original strand is preserved even after amplification. This may be achieved by for example the following ways:

1) by ligation of Y-shaped adapters to ds polynucleotide with differentiating strands, where Y-shaped adapters comprise a complementary double stranded sequence (e.g. ~13 nt long) which ligates to the ds DNA, and further comprises at least one single stranded tail (e.g. 20 nt long) of a different sequence. After ligation of such adapters 5'ends of each strand in ds cDNA fragment are specifically marked with the same sequence, different from that attached to the 3' ends. The adapter sequences correspond to primer sequences used later in the procedure. After selection of the strand for amplification, where the other one is either removed, or destroyed or incapable to be amplified due to sensitivity of the polymerase used to the at least one modified nucleotide, the amplification is carried out with the selected strand, wherein 5' and 3' ends bear different sequences for PCR primers (FIG. 2A-1).
2) By ligation of directional adapters (FIG. 2A-2)
3) by ligation of two types of at least partly ds adapters to the ds polynucleotide; wherein one of the strands of one of adapters bears at least one biotinylated nucleotide. Through the biotin group, ds DNA with at least one biotinylated adapter is attached to streptavidine coated beads, and the non-biotinylated strand is washed away, leaving on the beads only biotinylated strand which may be with and without modified nucleotides. Then the strand for amplification is selected, while the other one is either removed, or destroyed or incapable to be amplified due to sensitivity of the polymerase used to the at least one modified nucleotide, and amplified with primers corresponding to the adapters sequences. Since the biotinylated adapter is known (whether it is attached to 5' or 3' end of the selected strand), the polarity of the selected strand is preserved after amplification (FIG. 2A-3). Instead of biotin, it is possible to use any chemical group capable to bind to some surface and not interfering with amplification.

The term PCR refers to polymerase chain reaction. This is a general term comprising all protocols, conditions, automatized and half-automatized devices in which at least one DNA template is amplified by default by means of a enzyme with polymerase activity. In general, such molecules with polymerase activity are enzymes such as Taq DNA polymerase, Pfu DNA polymerase, Phusion DNA polymerase, wherein Taq and Phusion DNA Polymerases are preferred.

It is particularly preferred that the at least one modified nucleotide is dUTP and said amplification is a Pfu DNA polymerase-dependent amplification.

If an amplification step is carried out in any of the embodiments of this invention a useful PCR (polymerase chain reaction) protocol shall be used by means of which the remaining intact DNA strand shall be amplified. Suitable PCR protocols of the include the known protocols for Standard PCR, Allele-Specific PCR, Alu PCR, Assembly PCR, Asymmetric PCR, Helicase Dependent Amplification HDA, Hot Start PCR, Inverse PCR, Intersequence-Specific PCR (ISSR PCR), Late-PCR, Ligation-mediated PCR, Long PCR, Methylation-Specific PCR, Miniprimer PCR, Multiplex PCR, Nested PCR, Overlap-Extension PCR, Quantitative PCR, Real Time PCR, Solid Phase PCR, Thermal Assymetric Interlaced PCR (TAIL-PCR), Touchdown PCR or combinations thereof. Preferred is the use of Standard PCR.

Herein the term "at least one intact DNA strand" means that the number of the intact DNA strands to be amplified can vary from one to many billions of different polynucleotides.

Figure 6:
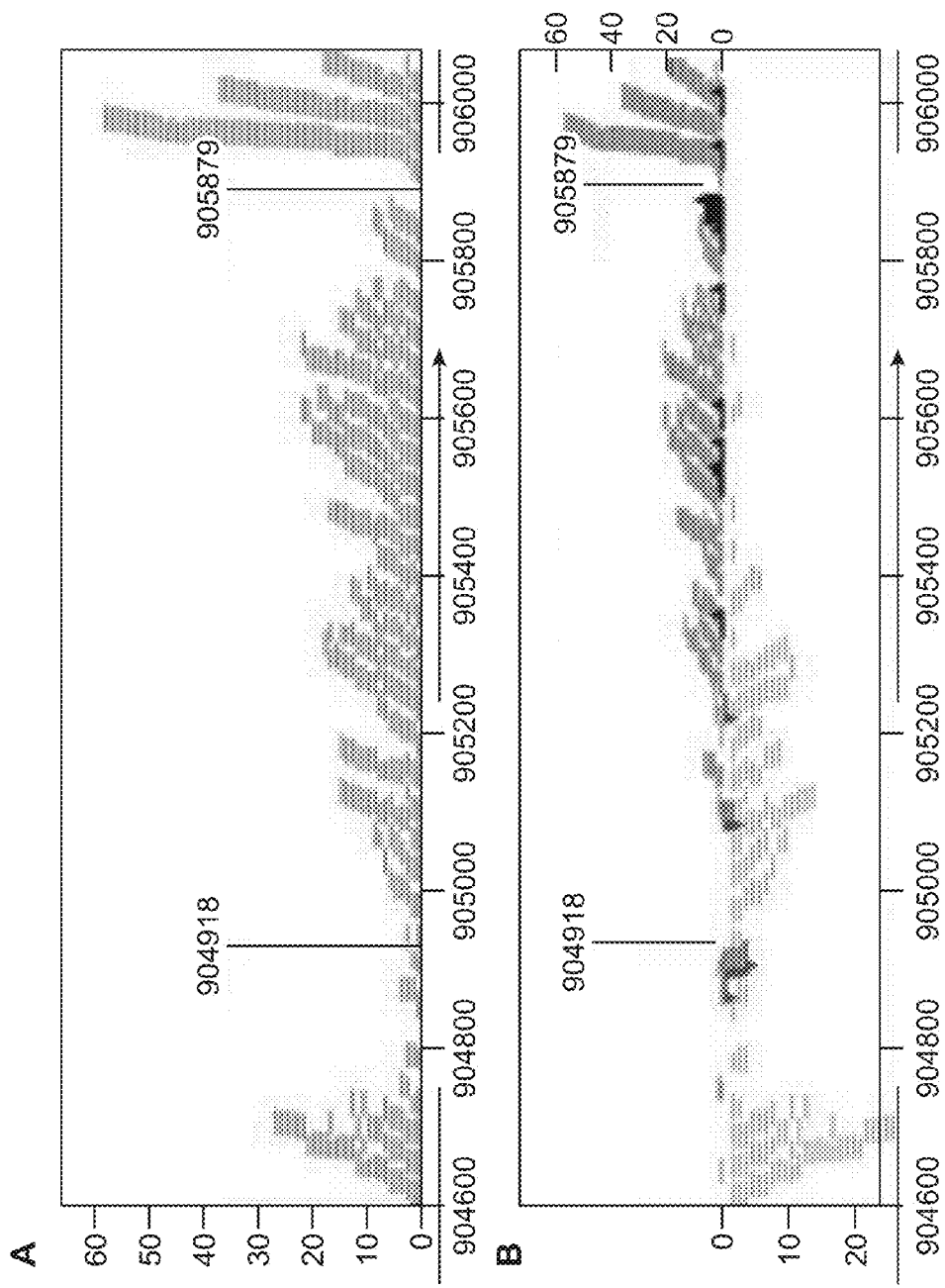

In a further optional step the resulting sequences can be aligned with already known sequence patterns of the corresponding DNA, if applicable. Such results can be plotted in a way such as shown in FIG. 6.

Optionally, the method according to the invention comprises the step of contig (contiguous) construction from the obtained sequences. Herein the sequences of different overlapping (contiguous) DNA fragments derived from the same source can be used for (re-)constructing the original respectively complete DNA sequence of this source.

Alternatively to the amplification step the at least one intact DNA strand can be hybridized to a nucleic acid structure displaying an antisense sequence of the at least one intact DNA strand. Suitable hybridization methods include in situ hybridization (hybridization of a DNA to a complementary sequence in isolated cells and/or tissues), Southern Blot (a method for verifying the presence of a DNA sequence in a DNA sample by separating the DNAs in the sample by size using gel electrophoresis and bringing said sample to a filter membrane for probe hybridization), Northern Blot (the equivalent of Southern Blot with RNA samples) and Southwestern Blot (identifying the presence of a DNA sequence in a DNA sample prepared according to the Southern blot method by hybridizing the sample on a nitrocellulose gel with characterizing DNA-binding proteins) microarray hybridization and correspondent "reverse" hybridizations were intact DNA's are loaded on a membrane and hybridised with particular probes.

When an amplification is intended the key steps of the inventive method are to be read in the following order:
I) Providing polynucleotide templates, primers, buffer solution(s), at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on the polynucleotide templates, so that double-stranded polynucleotides each consisting of a template and a matching strand are generated, wherein the matching strand contains the at least one modified nucleotide;
III) If said polynucleotide templates on step I) are single-stranded RNA, second-strand synthesis with unmodified dNTPs or corresponding analogues thereof is performed;
IV) Mark differently the 5' and 3' ends of the ds cDNA to preserve the polarity of the original strand after amplification;
V) Optionally, performing one or more molecular cloning operations on the double-stranded DNA, wherein the molecular cloning operations are selected from shearing, restriction, digestion, end-polishing, A-tailing, G-tailing and adaptor ligation;
VI) Amplifying the at least one remaining intact cDNA strand by performing PCR, whereby the other strand is removed, or destroyed or incapable to be amplified due to the at least one modified nucleotide.

The afore-mentioned method further comprises preferably the step of:
VII) Specific selection of at least one of the strands of the said polynucleotide duplex using different interaction of modified and unmodified nucleotides with at least one selection factor.

In the particularly preferred embodiment 1 of the method according to the invention a strand specific cloning of RNAs such as a whole transcriptome of a cell or a tissue shall be carried out. Therefore, at least one single strand RNA is provided, for example by isolation from the respective cell or tissue. The four dNTPs dATP, dCTP, dGTP and dTTP are added in sufficient amounts, i.e. amounts which allow performance of the inventive method, to the solution containing the at least one RNA strand. Then, a first cDNA strand is generated by using random primers (or oligo(dT), oligo (dU), oligo (U) primers) for annealing to said at least one RNA strand and an enzyme with Reverse Transcriptase activity. In the following at least one of the aforesaid dNTPs is replaced by at least one corresponding modified dNTP. For example, the modified dNTP may be a dNTP which can be specifically degraded by adding a degrading agent in order that the strand containing the such degraded at least one modified dNTP is not suitable anymore for amplification, or the modified dNTP may expose the such marked cDNA strand for being removed by interaction with specific agents interacting with the additional functional group or groups on the at least one modified dNTP. With the four dNTPs including the at least one modified dNTP second strand cDNA synthesis is performed by using the first cDNA strand as a matrix and a suitable enzyme with polymerase activity. In the next step polarity specific adaptors are ligated to the ends of cDNA strands, allowing a polymerase to dock to the adaptor structure for PCR amplification. After the ligation the second cDNA strand containing the at least one modified dNTP is for example degraded by degrading the at least one modified dNTP with a suitable degrading agent, or the at least one second cDNA strand containing the at least one modified dNTP is separated from the at least one first cDNA strand by special molecules or particles attaching to characteristic structures on the modified dNTP. Finally, the remaining intact first cDNA strand is amplified by PCR using a suitable enzyme with polymerase activity.

Thus the steps of this embodiment of the inventive method can be summarized in the following schematic order:
1) Providing at least one single-stranded RNA molecule;
2) Adding sufficient amounts of the four dNTPs dATP, dCTP, dGTP and dTTP or corresponding analogues thereof;
3) Generating a first cDNA strand;
4) Replacing at least one dNTP with at least one corresponding modified dNTP;
5) Performing second-strand synthesis on the first cDNA strand;

6) Ligating polarity-specific adaptors to one or both ends of the cDNA double strand;
7) Specifically modifying or removing the second cDNA strand containing the at least one modified dNTP; and
8) Amplifying the at least one remaining intact cDNA strand by performing PCR.

In embodiment 2 strand specific cloning of RNA can be achieved also by varying the steps of the inventive method. In this embodiment the first cDNA strand shall contain the at least one modified dNTP. In the replacement step this at least one modified dNTP is substituted by the corresponding classic dNTP. Thus in this embodiment the at least one first cDNA strand will be either degraded or removed. The amplification step is then performed on the remaining intact second cDNA strand. All other steps are adjusted correspondingly.

The steps of this embodiment of the inventive method can be summarized in the following schematic order:
1) Providing at least one single-stranded RNA molecule;
2) Adding sufficient amounts of the four dNTPs dATP, dCTP, dGTP and dTTP or corresponding analogues thereof, wherein at least one of the four dNTPs is a modified dNTP;
3) Generating a first cDNA strand;
4) Replacing the at least one modified dNTP with the corresponding dNTPs or analogues of the corresponding dNTPs;
5) Performing second-strand synthesis on the first cDNA strand;
6) Ligating polarity-specific adaptors to one or both ends of the cDNA double strand;
7) Specifically modifying or removing the first cDNA strand containing the at least one modified dNTP; and
8) Amplifying the at least one remaining intact cDNA strand by performing PCR.

In embodiment 3 strand specific selection according to the invention can also be achieved using single-stranded DNA as a template. Here at least one DNA single strand is provided. A cDNA strand is synthesized wherein at least one modified dNTP is integrated. In this embodiment only one cDNA strand is synthesized since a second cDNA strand would be identical to the original DNA single strand. Finally, the original single-stranded DNA shall be amplified. Thus all transcripts resulting from the PCR will bear the same reading direction of the sequence as the original single-stranded DNA. The other steps are adjusted accordingly.

This leads to the following schematic order:
1) Providing at least one single-stranded DNA molecule;
2) Adding sufficient amounts of the four dNTPs dATP, dCTP, dGTP and dTTP or corresponding analogues thereof, wherein at least one of the four dNTPs is a modified dNTP used for the strand specific differentiation;
3) Generating a cDNA strand;
4) Ligating polarity-specific adaptors to one or both ends of the resulting DNA double strand;
5) Specifically modifying or removing the cDNA strand containing the at least one modified dNTP; and
6) Amplifying the at least one intact DNA strand by performing PCR.

In embodiment 4 the purpose of the inventive method is not an amplification but a hybridization. This hybridization can occur against any structure carrying a corresponding antisense sequence to the at least one intact first cDNA strand (see below). For a hybridization without amplification no adaptors have to be ligated. Consequently, this step is omitted in this embodiment and the amplification step is replaced by a hybridization step. Thus the order of the steps of the inventive method reads as follows:
1) Providing at least one single-stranded RNA molecule;
2) Adding sufficient amounts of the four dNTPs dATP, dCTP, dGTP and dTTP or corresponding analogues thereof;
3) Generating a first cDNA strand;
4) Replacing at least one dNTP with at least one corresponding modified dNTP used for the strand specific differentiation;
5) Performing second-strand synthesis on the first cDNA strand;
6) Specifically modifying or removing the second cDNA strand containing the at least one modified dNTP; and
7) Hybridizing the at least one remaining intact cDNA strand to a suitable antisense DNA sequence.

Embodiment 5 varies embodiment 4 in so far that herein the first cDNA strand contains the at least one modified dNTP. Thus the remaining intact second cDNA strand is hybridized. Consequently, the sequence against which the remaining intact second cDNA strand is hybridized must display an antisense sequence of the second strand. The steps of the inventive method are adjusted according to embodiments 2 and 4 and read as follows:
1) Providing at least one single-stranded RNA molecule;
2) Adding sufficient amounts of the four dNTPs dATP, dCTP, dGTP and dTTP or corresponding analogues thereof, wherein at least one of the four dNTPs is a modified dNTP used for the strand specific differentiation;
3) Generating a first cDNA strand;
4) Replacing the at least one modified dNTP with the corresponding dNTPs or analogues of the corresponding dNTPs;
5) Performing second-strand synthesis on the first cDNA strand;
6) Specifically modifying or removing the first cDNA strand containing the at least one modified dNTP; and
7) Hybridizing the at least one remaining intact cDNA strand to a suitable antisense DNA sequence.

In embodiment 6 the hybridization step follows after an amplification step. In various hybridization modes it may be advantageous to hybridize not only one or a few copies of the respective intact cDNA strand, but a large number as resulting from an amplification. Thus the steps of ligating a polarity-specific adaptor and of an amplification have to be integrated again. The order of the steps reads like embodiment 1 and a subsequent hybridization step:
1) Providing at least one single-stranded RNA molecule;
2) Adding sufficient amounts of the four dNTPs dATP, dCTP, dGTP and dTTP or corresponding analogues thereof;
3) Generating a first cDNA strand;
4) Replacing at least one dNTP with at least one corresponding modified dNTP;
5) Performing second-strand synthesis on the first cDNA strand;
6) Ligating polarity-specific adaptors to one or both ends of the cDNA double strand;
7) Specifically modifying or removing the second cDNA strand containing the at least one modified dNTP; and
8) Amplifying the at least one remaining intact cDNA strand by performing PCR.
9) Hybridizing the amplified cDNA to a suitable antisense DNA sequence.

Correspondingly, in embodiment 7 the hybridization step can ensue after performing an amplification of the intact second-strand cDNA, as in embodiment 2:
1) Providing at least one single-stranded RNA molecule;
2) Adding sufficient amounts of the four dNTPs dATP, dCTP, dGTP and dTTP or corresponding analogues thereof, wherein at least one of the four dNTPs is a modified dNTP;
3) Generating a first cDNA strand;
4) Replacing the at least one modified dNTP with the corresponding dNTPs or analogues of the corresponding dNTPs;
5) Performing second-strand synthesis on the first cDNA strand;
6) Ligating polarity-specific adaptors to one or both ends of the cDNA double strand;
7) Specifically modifying or removing the first cDNA strand containing the at least one modified dNTP; and
8) Amplifying the at least one remaining intact cDNA strand by performing PCR.
9) Hybridizing the amplified cDNA to a suitable antisense DNA sequence.

Also in the case of single-stranded DNA it may be advantageous to combine an amplification and a hybridization step. Thus in embodiment 8 the order of the steps reads as follows:
1) Providing at least one single-stranded DNA molecule;
2) Adding sufficient amounts of the four dNTPs dATP, dCTP, dGTP and dTTP or corresponding analogues thereof, wherein at least one of the four dNTPs is a modified dNTP used for the strand specific differentiation;
3) Generating a cDNA strand;
4) Ligating polarity-specific adaptors to one or both ends of the resulting DNA double strand;
5) Specifically modifying or removing the cDNA strand containing the at least one modified dNTP; and
6) Amplifying the at least one intact DNA strand by performing PCR.
7) Hybridizing the amplified DNA to a suitable antisense DNA sequence.

Embodiment 9: If the sequence of the original RNA is not known it may be desirable to perform sequencing. Thus such a step is added to the step order of embodiment 1:
1) Providing at least one single-stranded RNA molecule;
2) Adding sufficient amounts of the four dNTPs dATP, dCTP, dGTP and dTTP or corresponding analogues thereof;
3) Generating a first cDNA strand;
4) Replacing at least one dNTP with at least one corresponding modified dNTP;
5) Performing second-strand synthesis on the first cDNA strand;
6) Ligating polarity-specific adaptors to one or both ends of the cDNA double strand;
7) Specifically modifying or removing the second cDNA strand containing the at least one modified dNTP; and
8) Optionally, amplifying the at least one remaining intact cDNA strand by performing PCR.
9) Sequencing the resulting copies of the at least one intact cDNA strand.

Embodiment 10: Consequently, it is also possible to include a sequencing step if the first-stranded included the at least one modified dNTP and the intact second-strand cDNA is amplified, as in embodiment 2:
1) Providing at least one single-stranded RNA molecule;
2) Adding sufficient amounts of the four dNTPs dATP, dCTP, dGTP and dTTP or corresponding analogues thereof, wherein at least one of the four dNTPs is a modified dNTP;
3) Generating a first cDNA strand;
4) Replacing the at least one modified dNTP with the corresponding dNTPs or analogues of the corresponding dNTPs;
5) Performing second-strand synthesis on the first cDNA strand;
6) Ligating polarity-specific adaptors to one or both ends of the cDNA double strand;
7) Specifically modifying or removing the first cDNA strand containing the at least one modified dNTP; and
8) Optionally, amplifying the at least one remaining intact cDNA strand by performing PCR.
9) Sequencing the resulting copies of the at least one intact cDNA strand.

Embodiment 11: After sequencing it may be desirable to determine the polarity of the resulting sequence(s). This may serve for several analytic or diagnostic purposes (see below) or for aligning RNA transcripts to gene sequences known from DNA sequencing projects. If the remaining intact first strand cDNA was sequenced the order of the steps of the inventive method read as follows:
1) Providing at least one single-stranded RNA molecule;
2) Adding sufficient amounts of the four dNTPs dATP, dCTP, dGTP and dTTP or corresponding analogues thereof;
3) Generating a first cDNA strand;
4) Replacing at least one dNTP with at least one corresponding modified dNTP;
5) Performing second-strand synthesis on the first cDNA strand;
6) Ligating polarity-specific adaptors to one or both ends of the cDNA double strand;
7) Specifically modifying or removing the second cDNA strand containing the at least one modified dNTP; and
8) Optionally, amplifying the at least one remaining intact cDNA strand by performing PCR.
9) Sequencing the resulting copies of the at least one intact cDNA strand.
10) Aligning of sequencing reads to the reference genome or reconstructing of the RNA sequence from individual sequencing reads.
11) Determining the polarity of the at least one RNA transcript.

Embodiment 12: Consequently, such a determination of the polarity and optionally an alignment to a gene structure known from a sequencing project can also be performed if the remaining intact second strand cDNA was amplified and sequenced. As in this case the antisense sequence is resulting the sequence has to be inverted, preferably by means of a computer programme, into the correct reading sequence.

Thus the order of the steps of the inventive method is:
1) Providing at least one single-stranded RNA molecule;
2) Adding sufficient amounts of the four dNTPs dATP, dCTP, dGTP and dTTP or corresponding analogues thereof, wherein at least one of the four dNTPs is a modified dNTP;
3) Generating a first cDNA strand;
4) Replacing the at least one modified dNTP with the corresponding dNTPs or analogues of the corresponding dNTPs;
5) Performing second-strand synthesis on the first cDNA strand;

6) Ligating polarity-specific adaptors to one or both ends of the cDNA double strand;
7) Specifically modifying or removing the first cDNA strand containing the at least one modified dNTP; and
8) Optionally, amplifying the at least one remaining intact cDNA strand by performing PCR;
9) Sequencing the resulting copies of the at least one intact cDNA strand;
10) Aligning of sequencing reads to the reference genome or reconstructing of the RNA sequence from individual sequencing reads;
11) Determining the polarity of the at least one RNA transcript Embodiment 13: In analogy, it may be also desirable to sequence the amplified copies of a single-stranded DNA if the sequence isn't known yet. Thus a sequencing step ensues to the order of the steps of the inventive method of embodiment 3:
1) Providing at least one single-stranded DNA molecule;
2) Adding sufficient amounts of the four dNTPs dATP, dCTP, dGTP and dTTP or corresponding analogues thereof, wherein at least one of the four dNTPs is a modified dNTP used for the strand specific differentiation;
3) Generating a cDNA strand;
4) Ligating polarity-specific adaptors to one or both ends of the resulting DNA double strand;
5) Specifically modifying or removing the cDNA strand containing the at least one modified dNTP; and
6) Optionally, amplifying the at least one intact DNA strand by performing PCR.
7) Sequencing the resulting copies of the at least one intact DNA strand.

Embodiment 14: Also for single-stranded DNA it may be desirable to determine the polarity of the resulting copies after amplification and sequencing. As for single-stranded DNA by needs only one cDNA strand is generated including the at least one modified dNTP the resulting sequence must be inverted, as in embodiment 12.
1) Providing at least one single-stranded DNA molecule;
2) Adding sufficient amounts of the four dNTPs dATP, dCTP, dGTP and dTTP or corresponding analogues thereof, wherein at least one of the four dNTPs is a modified dNTP used for the strand specific differentiation;
3) Generating a cDNA strand;
4) Ligating polarity-specific adaptors to one or both ends of the resulting DNA double strand;
5) Specifically modifying or removing the cDNA strand containing the at least one modified dNTP; and
6) Optionally, amplifying the at least one intact DNA strand by performing PCR;
7) Sequencing the resulting copies of the at least one intact DNA strand;
8) Aligning of sequencing reads to the reference genome or reconstructing of the DNA sequence from individual sequencing reads;
9) Determining the polarity of the at least one DNA molecule.

In another preferred embodiment 15 the original polynucleotide strand is a double-stranded DNA. Herein it may be necessary to set a nick into the particular strand of the double-stranded DNA which shall be substituted. A possible sequence of the steps according to this embodiment is:
1) Providing at least one double-stranded DNA;
2) Setting a nick in one particular strand of the double-stranded DNA by using a nicking endonuclease;
3) Adding sufficient amounts of the four dNTPs dATP, dCTP, dGTP and dTTP or corresponding analogues thereof, wherein at least one of the four dNTPs is a modified dNTP used for the strand specific differentiation;
4) Performing nick-translation of the nicked DNA strand by means of a DNA polymerase with 5' to 3' exonuclease activity;
5) Specifically modifying or removing the cDNA strand containing the at least one modified dNTP.

In a further preferred embodiment 16 the original polynucleotide strand is a double-stranded DNA obtained as a result of PCR reaction. A special modified nucleotide is introduced into one PCR primer to set a nick into the particular strand of the double-stranded DNA which shall be substituted. A possible sequence of the steps according to this embodiment is:
1) Providing at least one double-stranded DNA obtained in PCR reaction where one of PCR-primers contains dUTP;
2) Setting a nick in one particular strand of the double-stranded DNA by UNG treatment and APE 1 digestion or UNG treatment and alkalic hydrolisis;
3) Adding sufficient amounts of the four dNTPs dATP, dCTP, dGTP and dTTP or corresponding analogues thereof, wherein at least one of the four dNTPs is a modified dNTP used for the strand specific differentiation;
4) Performing nick-translation of the nicked DNA strand by means of a DNA polymerase with 5' to 3' exonuclease activity;
5) Specifically modifying or removing the cDNA strand containing the at least one modified dNTP.

Embodiment 17: In another preferred embodiment the method according to the invention is performed in the following way:
1) Providing at least one single-stranded RNA molecule;
2) Adding sufficient amounts of the four dNTPs dATP, dCTP, dGTP and dTTP or corresponding analogues thereof, wherein at least one of the four dNTPs is a modified dNTP;
3) Generating a first cDNA strand, wherein at least one nucleotide is a modified dNTP;
4) Replacing the at least one modified dNTP with the corresponding dNTPs or analogues of the corresponding dNTPs;
5) Performing second-strand synthesis on the first cDNA strand;
6) Specifically modifying or removing the first cDNA strand containing the at least one modified dNTP; and Embodiment 18: In another preferred embodiment the method according to the invention is performed in the following way:
1) Providing at least one single-stranded RNA molecule;
2) Adding sufficient amounts of the four dNTPs dATP, dCTP, dGTP and dTTP or corresponding analogues thereof;
3) Generating a first cDNA strand,
4) Replacing at least one dNTP with at least one corresponding modified dNTP;
5) Performing second-strand synthesis on the first cDNA strand, generating a second cDNA strand, wherein at least one nucleotide is a modified dNTP;
6) Specifically modifying or removing the second cDNA strand containing the at least one modified dNTP.

Embodiment 19: In another preferred embodiment the method according to the invention is performed in the following way:
1) Performing first-strand synthesis on a polynucleotide template by providing polynucleotide template, primers, correspondent buffer, polymerase and sufficient amounts of the four dNTPs: dATP, dCTP, dGTP and dTTP or corresponding analogues thereof, wherein at least one of the four dNTPs is a modified nucleotide used for strand specific selection, so that a double-stranded polynucleotide comprising a template a matching strand containing the at least one modified nucleotide is generated;
2) Optionally, second-strand synthesis with unmodified dNTPs or corresponding analogues thereof, if said polynucleotide template on step I) is a single-stranded RNA;
3) Optionally, performing molecular cloning operations with double-stranded DNA; and
4) Strand specific selection using different interaction of modified and unmodified nucleotides with some selection factor.

The inventive method for selection of a particular strand where the preservation of information about the direction is desired after being transformed into a double-stranded form comprises also the following steps:
I) Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on the polynucleotide templates, so that double-stranded polynucleotides each consisting of a template and a matching strand are generated, wherein the matching strand contains the at least one modified nucleotide;
III) If said polynucleotide templates on step I) are single-stranded RNA, second-strand synthesis with unmodified dNTPs or corresponding analogues thereof is performed;
IV) Optionally, performing molecular cloning operations with double-stranded DNA; and
V) Specific selection of at least one of the strands of the said polynucleotide duplex using different interaction of modified and unmodified nucleotides with at least one selection factor.

The inventive method for selection of a single stranded RNA from a double stranded polynucleotide comprises the following steps:
I) Providing RNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on the RNA templates, so that double-stranded polynucleotides each consisting of a template and a matching strand are generated, wherein the matching strand contains the at least one modified nucleotide;
III) Performing second-strand synthesis with unmodified dNTPs or corresponding analogues thereof;
IV) Optionally, performing molecular cloning operations with double-stranded DNA; and
V) Specific selection of at least one of the strands of the said polynucleotide duplex using different interaction of modified and unmodified nucleotides with at least one selection factor.

The inventive method for selection of a single stranded RNA from a double stranded polynucleotide can also comprise the following steps:
I) Providing RNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on the RNA templates with unmodified dNTPs or corresponding analogues thereof;
III) Performing second-strand synthesis wherein at least one of the four dNTPs is replaced by a corresponding modified dNTP used for strand-specific selection, so that double-stranded polynucleotides each consisting of a template and a matching strand are generated, wherein the template contains the at least one modified nucleotide;
IV) Optionally, performing molecular cloning operations with double-stranded DNA; and
V) Specific selection of at least one of the strands of the said polynucleotide duplex using different interaction of modified and unmodified nucleotides with at least one selection factor.

The inventive method for selection of a single stranded DNA from a double stranded polynucleotide comprises the following steps:
I) Providing DNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on the DNA templates, so that double-stranded polynucleotides each consisting of a template and a matching strand are generated, wherein the matching strand contains the at least one modified nucleotide;
III) Optionally, performing molecular cloning operations with double-stranded DNA; and
VI) Specific selection of at least one of the strands of the said polynucleotide duplex using different interaction of modified and unmodified nucleotides with at least one selection factor.

The inventive method for selection of a single stranded RNA from a double stranded DNA/RNA hybrid comprises the following steps:
I) Providing DNA/RNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
II) Performing first-strand synthesis on the RNA templates, so that double-stranded polynucleotides each consisting of a template and a matching strand are generated, wherein the matching strand contains the at least one modified nucleotide;
III) Performing second-strand synthesis with unmodified dNTPs or corresponding analogues thereof;
IV) Optionally, performing molecular cloning operations with double-stranded DNA; and V) Specific selection of at least one of the strands of the said polynucleotide duplex using different interaction of modified and unmodified nucleotides with at least one selection factor.

The inventive method for selection of a single stranded RNA from a double stranded DNA/RNA hybrid comprises the following steps:
  I) Providing DNA/RNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
  II) Performing first-strand synthesis on the RNA templates with unmodified dNTPs or corresponding analogues thereof;
  III) Performing second-strand synthesis wherein at least one of the four dNTPs is replaced by a corresponding modified dNTP used for strand-specific selection, so that double-stranded polynucleotides each consisting of a template and a matching strand are generated, wherein the template contains the at least one modified nucleotide;
  IV) Optionally, performing molecular cloning operations with double-stranded DNA; and
  V) Specific selection of at least one of the strands of the said polynucleotide duplex using different interaction of modified and unmodified nucleotides with at least one selection factor.

The inventive method for selection of a single stranded DNA from a double stranded DNA/RNA hybrid comprises the following steps:
  I) Providing DNA/RNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
  II) Performing first-strand synthesis on the DNA templates, so that double-stranded polynucleotides each consisting of a template and a matching strand are generated, wherein the matching strand contains the at least one modified nucleotide;
  III) Optionally, performing molecular cloning operations with double-stranded DNA; and
  VI) Specific selection of at least one of the strands of the said polynucleotide duplex using different interaction of modified and unmodified nucleotides with at least one selection factor.

The inventive method for selection of a single stranded DNA from a double stranded DNA/RNA hybrid comprises the following steps:
  I) Providing DNA/RNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
  II) Performing first-strand synthesis on the DNA templates with unmodified dNTPs or corresponding analogues thereof;
  III) Performing second-strand synthesis wherein at least one of the four dNTPs is replaced by a corresponding modified dNTP used for strand-specific selection, so that double-stranded polynucleotides each consisting of a template and a matching strand are generated, wherein the template contains the at least one modified nucleotide;
  III) Optionally, performing molecular cloning operations with double-stranded DNA; and
  VI) Specific selection of at least one of the strands of the said polynucleotide duplex using different interaction of modified and unmodified nucleotides with at least one selection factor.

The inventive method for selection of a single stranded DNA from a double stranded polynucleotide can also comprise the following steps:
  I) Providing DNA templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
  II) Performing first-strand synthesis on the DNA templates with unmodified dNTPs or corresponding analogues thereof;
  III) Performing second-strand synthesis wherein at least one of the four dNTPs is replaced by a corresponding modified dNTP used for strand-specific selection, so that double-stranded polynucleotides each consisting of a template and a matching strand are generated, wherein the template contains the at least one modified nucleotide;
  IV) Optionally, performing molecular cloning operations with double-stranded DNA; and
  V) Specific selection of at least one of the strands of the said polynucleotide duplex using different interaction of modified and unmodified nucleotides with at least one selection factor.

The inventive method for selection of a particular strand from a double stranded polynucleotide can further also comprise or consist of the following steps:
  I) Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;
  II) Performing first-strand synthesis on the polynucleotide templates with unmodified dNTPs or corresponding analogues thereof;
  III) Performing second-strand synthesis wherein at least one of the four dNTPs is replaced by a corresponding modified dNTP used for strand-specific selection, so that double-stranded polynucleotides each consisting of a template and a matching strand are generated, wherein the template contains the at least one modified nucleotide;
  IV) Optionally, performing molecular cloning operations with double-stranded DNA; and
  V) Specific selection of at least one of the strands of the said polynucleotide duplex using different interaction of modified and unmodified nucleotides with at least one selection factor.

The inventive method for selection of a particular strand from a double stranded polynucleotide can further also comprise or consist of the following steps:
  I') Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;

IIa') Performing first-strand synthesis on the polynucleotide templates with unmodified dNTPs or corresponding analogues thereof;

or

IIb') Performing first-strand synthesis on the polynucleotide templates, so that double-stranded polynucleotides each consisting of a template and a matching strand are generated, wherein the matching strand contains the at least one modified nucleotide;

IIIa') If step IIa' was performed, second-strand synthesis is performed wherein at least one of the four dNTPs is replaced by a corresponding modified dNTP used for strand-specific selection, so that double-stranded polynucleotides each consisting of a template and a matching strand are generated, wherein the template contains the at least one modified nucleotide;

IIIb') If step IIb' was performed and said polynucleotide templates on step I) are single-stranded RNA, second-strand synthesis with unmodified dNTPs or corresponding analogues thereof is performed and IV') Optionally, performing molecular cloning operations with double-stranded DNA; and V') Specific selection of at least one of the strands of the said polynucleotide duplex using different interaction of modified and unmodified nucleotides with at least one selection factor.

In a further embodiment the inventive method comprises selecting in ds (double stranded) polynucleotides the strand with at least one modified nucleotide to distinguish the template from the matching strand, wherein the selected strand with the at least one modified nucleotide in ds (double stranded) polynucleotides can be removed or destroyed and the removed strand with the modified nucleotide can be used separately, whereby if the strand with the modified nucleotide is not removed and destroyed, it can remain in the same solution with the matching strand, wherein the modified nucleotide in the strand prevents the amplification of the strand comprising the following steps:

I) Providing polynucleotide templates, primers, buffer solution, at least one enzyme with polymerase activity, sufficient amounts of the four dNTPs dATP, dCTP, dGTP and dTTP or analogues thereof, wherein at least one of the four dNTPs is replaced by a corresponding modified dNTP used for strand-specific selection;

II) Performing first-strand synthesis on the polynucleotide templates, so that double-stranded polynucleotides each consisting of a template and a matching strand are generated, wherein the matching strand contains the at least one modified nucleotide;

III) If said polynucleotide templates on step I) are single-stranded RNA, second-strand synthesis with unmodified dNTPs or corresponding analogues thereof is performed;.;

IV) Optionally, performing molecular cloning operations with double-stranded DNA; and V) Specific selection of at least one of the strands of the said polynucleotide duplex using different interaction of modified and unmodified nucleotides with at least one selection factor.

It is obvious to a person skilled in the art that the different steps mentioned before in the respective embodiments can be combined for solving similar or different tasks provided the order and the selection of the different steps results in a meaningful order of the steps. All these possible combinations shall fall under the scope and the spirit of the invention.

By way of example, the method according to the invention was applied on the yeast transcriptome (Example 1). In a similar fashion, it was applied on the transcriptome of the mouse brain (Example 2). These two examples were chosen because comparative data from the Applicants' laboratory and other laboratories are available. Also complete genomes of these organisms are published. By way of comparing the results from conventional RNA-Seq and the inventive method according to the invention the advantages of the inventive method become apparent. As shown e.g. in Example 1 and FIG. 6, the inventive method allows a differentiation in sense and antisense transcripts. In this plot sense transcripts are marked in blue and antisense transcripts in red. Thus the method according to the invention can use the maintained information of the polarity of a transcript to generate more precise gene expression maps. Practical applications are discussed further below.

The reliability of the method according to the invention was validated in several control experiments. First, it was tested to which degree the inventive method can reproduce the results of conventional RNA sequencing. Herein the amplified sense and antisense transcripts according to the invention were pooled for allowing a correlation analysis. The results such as shown in Example 3 and FIG. 7A show a high correlation between the two methods. A high correlation corresponds to a distribution close to unity. A low correlation would be represented by a widely scattered distribution pattern. Thus the inventive method does not disturb the overall expression and transcriptome pattern in a sample. So the results of both methods can be compared to one another.

Next, two different strand-specific expression profilings were performed according to the invention on the same sample. Herein, only sense transcripts were included. The results were plotted again as described before. An excellent reproducibility of the inventive method is given, as can be seen in Example 4 and FIG. 7B.

In a further control experiment, the combination of sense and antisense transcripts obtained were compared to the results from another laboratory. There is still a very high correlation between the results, although with a somewhat broader scatter pattern (see Example 4 and FIG. 7C). Such a variation nearly always occurs when comparing the results from different laboratories. This experiment shows that this method does not work only under the specific conditions of the Applicants' laboratory, but can be universally used.

In order to test whether sense and antisense transcripts obtained according to the inventive method can be appropriately differentiated sense and antisense transcripts were compared and depicted in such an aforesaid scatter plot. As can be seen in FIG. 7D there is nearly no correlation. Thus sense and antisense transcripts obtained according to the inventive method are unequivocally different. This is a proof that the inventive method is highly suitable for differentiating accurately between sense and antisense transcripts.

The stability of the inventive method in respect of a complete exchange of at least one dNTP by at least one corresponding degradable analogue was tested. For this purpose in one reaction dTTP was exchanged by 100% dUTP. In another reaction dTTP was exchanged only by 75% dUTP, with 25% dTTP remaining in the reaction batch. The results from both experiments were compared for the sense transcripts and antisense transcripts (see Example 5 and FIG. 8). There is no significant deterioration in correlation when the exchange of the at least one dNTP was incomplete. When extrapolating these results it appears that only a part of the at least one dNTP must be replaced by the at least one corresponding degradable analogue to keep the method going with acceptable results, as shown in the correlation coefficient.

Actinomycin D is a substance which selectively inhibits DNA synthesis from DNA templates, but not from RNA templates. In a further experiment it could be shown that the presence of actinomycin D does not deteriorate significantly the results from the inventive protocol, neither for sense nor for antisense transcripts (see Example 6 and FIG. 9).

Practical applications of the inventive method include but are not limited to the provision of suitable kits for performing the inventive method according to the different protocols (embodiments) disclosed above.

FIG. 10 presents examples where information about transcription orientation helps to resolve overlaps of annotated and new genes in both yeast and mouse transcriptomes.

A kit in molecular biology is a package which includes all necessary ingredients for performing a certain method or singular step. Standard chemicals as present in any standard molecular biology laboratory are normally not included. Nevertheless some of these standard chemicals may be indispensable to carry out the inventive method properly. It is understood that all ingredients are provided in quantities that allow for a proper execution of the inventive method for the majority of scientific, diagnostic and industrial applications.

Often, but not always, these ingredients are provided in already prepared solutions ready- or close to ready-for-use. There may be also combinations of different ingredients already added together. A further advantage is that such kits use to be verified. Therefore the operator doesn't have to prove again the viability of the method and can save on at least some control experiments. Therefore kits are a very popular tool in molecular biology laboratories in research, diagnostics and industry.

For carrying out the key steps of the method according to the invention such a kit shall include the following components:
- A) All four dNTPs dATP, dCTP, dGTP and dTTP or corresponding analogues thereof, additionally at least one modified dNTP used for the strand specific selection;
- B) Primers
- C) One or more DNA polymerases;
- D) One or more degrading agents corresponding to the modified dNTPs and/or one or more removing agents apt for removing the strand containing the modified dNTPs.

If the protocol of the inventive method that shall be carried out includes an amplification step another embodiment of the kit should include:
- A) All four dNTPs dATP, dCTP, dGTP and dTTP or corresponding analogues thereof, additionally at least one modified dNTP used for the strand specific selection;
- B) Primers
- C) One or more DNA polymerases;
- D) One or more degrading agents corresponding to the modified dNTPs and/or one or more removing agents apt for removing the strand containing the modified dNTPs.
- E) One or more polarity-specific adaptor.

If the protocol of the inventive method that shall be carried out includes an amplification step and the original polynucleotide is a RNA another embodiment of the kit should include:
- A) All four dNTPs dATP, dCTP, dGTP and dTTP or corresponding analogues thereof, additionally at least one modified dNTP used for the strand specific selection;
- B) Primers
- C) One or more DNA polymerases;
- D) One or more degrading agents corresponding to the modified dNTPs and/or one or more removing agents apt for removing the strand containing the modified dNTPs.
- E) One or more polarity-specific adaptor;
- F) One or more Reverse transcriptases.

In any of the aforegoing kits according to the invention it may be preferable to include additionally components for removal of unmodified nucleotides by gel-filtration or purification on silica-column. Further kits are also preferred:

Kit A:
- A) All four dNTPs dATP, dCTP, dGTP and dTTP or corresponding analogues thereof, additionally at least one modified dNTP used for the strand specific selection;
- B) Primers
- C) One or more DNA polymerases;
- D) One or more degrading agents corresponding to the modified dNTPs and/or one or more removing agents apt for removing the strand containing the modified dNTPs;
- E) Components for specific removal of at least one modified or at least one unmodified nucleotide by gel-filtration or purification on silica-column.

Kit B:
- A) All four dNTPs dATP, dCTP, dGTP and dTTP or corresponding analogues thereof, additionally at least one modified dNTP used for the strand specific selection;
- B) Primers
- C) One or more DNA polymerases;
- D) One or more degrading agents corresponding to the modified dNTPs and/or one or more removing agents apt for removing the strand containing the modified dNTPs.
- E) One or more polarity-specific adaptor.
- F) Components for specific removal of at least one modified or at least one unmodified nucleotide by gel-filtration or purification on silica-column.

Kit C:
- A) All four dNTPs dATP, dCTP, dGTP and dTTP or corresponding analogues thereof, additionally at least one modified dNTP used for the strand specific selection;
- B) Primers
- C) One or more DNA polymerases;
- D) One or more degrading agents corresponding to the modified dNTPs and/or one or more removing agents apt for removing the strand containing the modified dNTPs.
- E) One or more polarity-specific adaptor;
- F) One or more Reverse transcriptases.
- G) Components for specific removal of at least one modified or at least one unmodified nucleotide by gel-filtration or purification on silica-column.

Kit D:
A kit for performing differentiation of polynucleotide strands comprising:
- A) All four dNTPs dATP, dCTP, dGTP and dTTP and corresponding modified deoxynucleotide;
- B) Primers;
- C) One or more DNA polymerases;
- D) One or more selection factors corresponding to the modified deoxynucleotide and/or one or more selective media for removing the strand containing the modified nucleotide;
- E) One or more DNA polymerases with reverse transcriptase activity;

Optionally comprising:
F) Components for specific removal of at least one modified or at least one unmodified nucleotide by gel-filtration or purification on silica-column.

Kit E:
A kit for ds cDNA synthesis from RNA preserving information about direction of original RNA strand comprising:
A) All four dNTPs dATP, dCTP, dGTP and dTTP/dUTP and at least one modified nucleotide corresponding to at least one from dATP, ATP, dCTP, CTP, dGTP, GTP, dTTP, TTP, dUTP and UTP;
B) Primers;
C) One or more DNA polymerases with reverse transcriptase activity;
D) One or more DNA polymerases; and
E) One or more selection factors suitable to specifically interact with said at least one modified nucleotide and/or one or more selective media for removing the strand containing the modified nucleotide;
Or additionally comprising
F) Components for specific removal of at least one modified or at least one unmodified nucleotide by gel-filtration or purification on silica-column.

To prevent spurious second-strand cDNA synthesis, which was shown to be the major source of artifactual antisense transcripts. Antisense artifacts in transcriptome microarray experiments are resolved by actinomycin D. Actinomycin D was included in the reverse transcription reaction. Actinomycin D specifically inhibits DNA-dependent, but not RNA-dependent, DNA synthesis. Actinomycin D is included in the kit to make the reaction more reproducible.

Thus in a preferred embodiment the kit also includes an inhibitor of DNA-dependent synthesis characterized in that said inhibitor does inhibit DNA-dependent, but not RNA-dependent, DNA synthesis.

Another application is the use of the results of this method for improved quantitative and qualitative diagnosis tests in selected diseases, as a part of the treatment or for prophylactic purposes. In general every disease is eligible which includes a temporary or permanent change in RNA expression levels. It is also possible to obtain a better monitoring of the effects of pharmaceutical agents used for therapy and/or prophylaxis of diseases provided these pharmaceutical agents produce a characteristic expression pattern different from that in untreated patients (humans or animals). Also improved gene expression patterns of plant, fungi, bacteria and viruses can be obtained by this method when the polarity of transcripts is available.

A further application is the production of improved and more selective microarrays. When the polarity of transcripts is known only the transcripts (respectively the antisense sequence) with a correct reading direction are meaningfully included in the microarray so that the limited space on the microarray is more economically used. Respectively, microarrays used for the generation of characteristic patterns instead of individual results may obtain a higher resolution by omitting non-characteristic transcripts of the incorrect reading direction.

As shown before, the advantages of the procedure according to the invention are providing a simple, inexpensive and reliable method for strand-specific cDNA cloning. This method is a novel and easy approach for determining the polarity of transcripts and using this information for purposes as outlined above. In particular, there is no need for the use of promoters or primer constructs containing promoter regions. The essence of the invention is the preservation of information about the direction of the original single-stranded molecules after being transformed into a double-stranded form or of particular strands in the original double stranded molecule and selection of the original strand according to the method of the invention. In a preferred embodiment the single-stranded molecule is a RNA and the double-stranded form a DNA.

Moreover, the method according to the invention has a higher accuracy in measuring expression levels of genes compared to RNA-Seq. Ignoring orientation of transcripts leads for example to overestimation of the expression level for about 10% of the mouse and about 15% of the yeast genes with noticeable expression level.

A further advantage of the method according to the invention is that the RNA is transcribed in cDNA and all the following steps are carried out with the cDNA which is much more resistant to degradation compared to RNA. In particular, strand specific differentiation is achieved by modifying a nucleotide in the cDNA and not in the RNA.

FIGURES

Figure 2B:
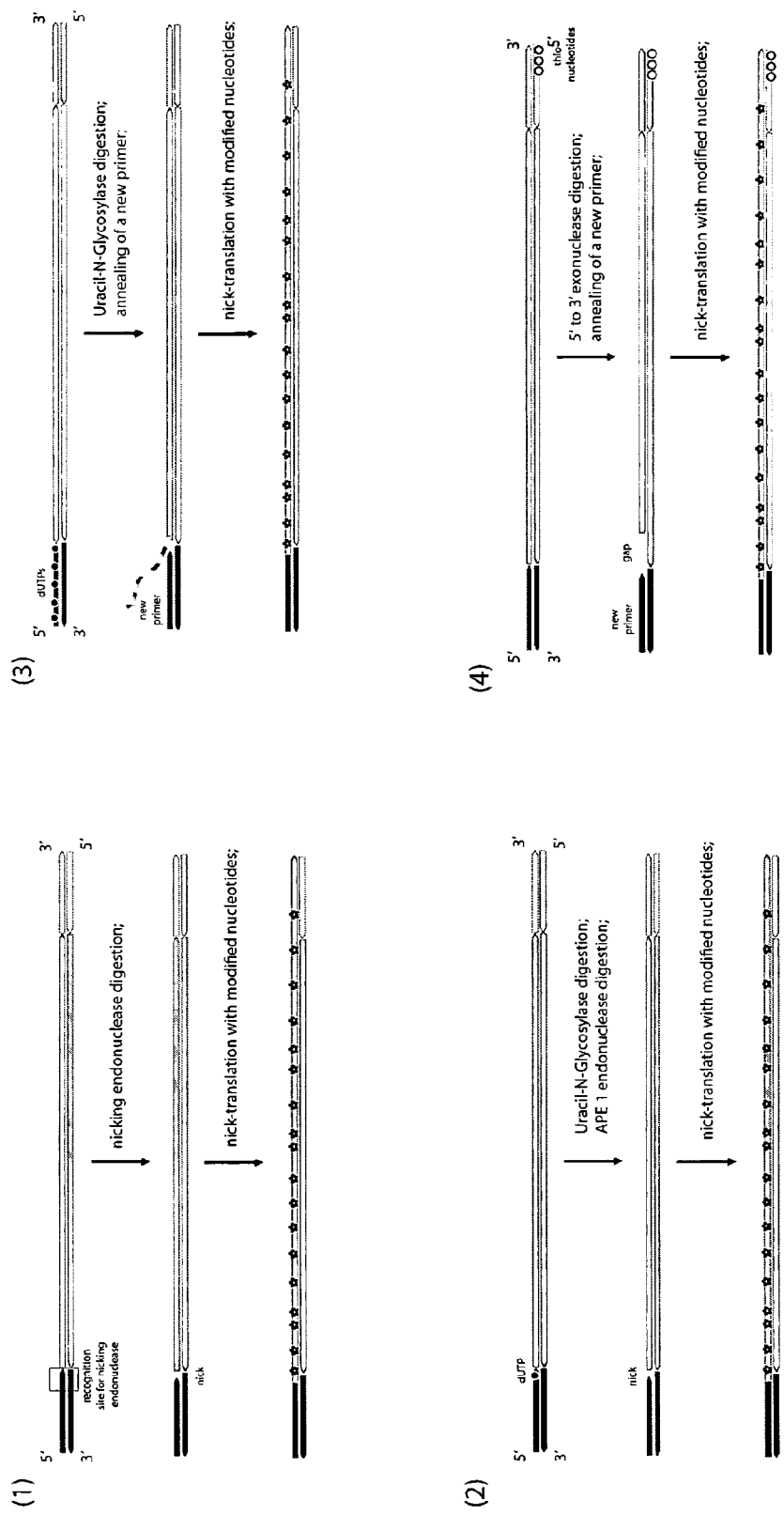

FIG. 1: Directional double-stranded DNA
(A) original single-stranded polynucleotide; (B) directional double-stranded DNA with distinguishable adaptors (state of the art); (C) directional double-stranded DNA with distinguishable strands; (D) directional double-stranded DNA with distinguishable strands and distinguishable adapters.

FIG. 2A: Conversion of distinguishable strands into distinguishable adaptors
(A1) Y-shaped adaptors are ligated to double-stranded DNA with distinguishable strands; modified strands are separated from unmodified ones; after synthesis of complementary strands or PCR-amplification double-stranded DNA with distinguishable adapters is generated.
(A2) directional adaptors are ligated to double-stranded DNA with distinguishable strands; modified strands are separated from unmodified ones; after PCR-amplification double-stranded DNA with distinguishable adapters is generated.
(A3) adaptors are ligated to double-stranded DNA with distinguishable strands, with one of adaptors bearing biotin in one of the strands. Streptavidine coated beads are used to fish out fragments, containing biotin. Uridine-containing strand is destroyed, remaining strand is amplified.

FIG. 2B: Conversion of distinguishable adaptors into distinguishable strands
(B1) nick introduced into one of the adaptors using nicking endonuclease;
(B2) dUTP in one of the adaptors is converted into a nick: Uracil-N-Glycosylase converts dUTP into an abasic site and APE 1 nuclease converts the abasic site into a nick;
(B3) double-stranded DNA is destabilized in one of the Uracil-N-Glycosylase; new primer is annealed in the destabilized region;
(B4) position for annealing of the primer is organized by action 5' to 3' exonuclease; another adapter is protected from action of 5' to 3' exonuclease by thio-nucleotides; nick-translation is performed by DNA polymerase I (or Taq polymerase) in presence of modified nucleotides.

Figure 3A:
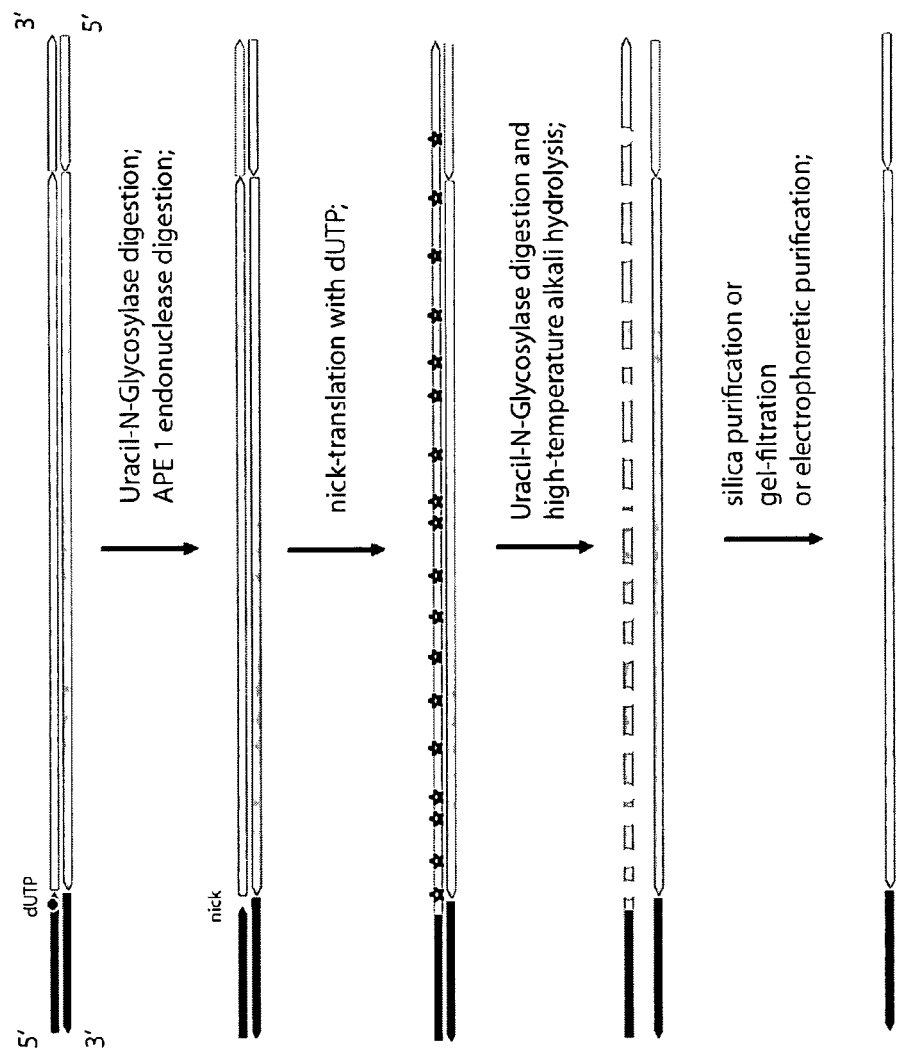

FIG. 3A: Preparation of single-stranded DNA according to the inventive method using dUTP as a modified nucleotide double-stranded DNA is a product of PCR reaction where one of the PCR-primers has dUTP at 3'-part;

dUTP in the PCR primer is converted into a nick: Uracil-N-Glycosylase converts dUTP into an abasic site and APE 1 nuclease converts the abasic site into a nick;

nick-translation is performed by DNA polymerase I (or Taq polymerase) in presence of dUTP;

dUTP-containing strand is destroyed by Uracil-N-Glycosylase digestion and alkali hydrolysis;

single-stranded DNA is purified by silica-based purification or gel-filtration or electrophoretic purification.

Figure 3B:
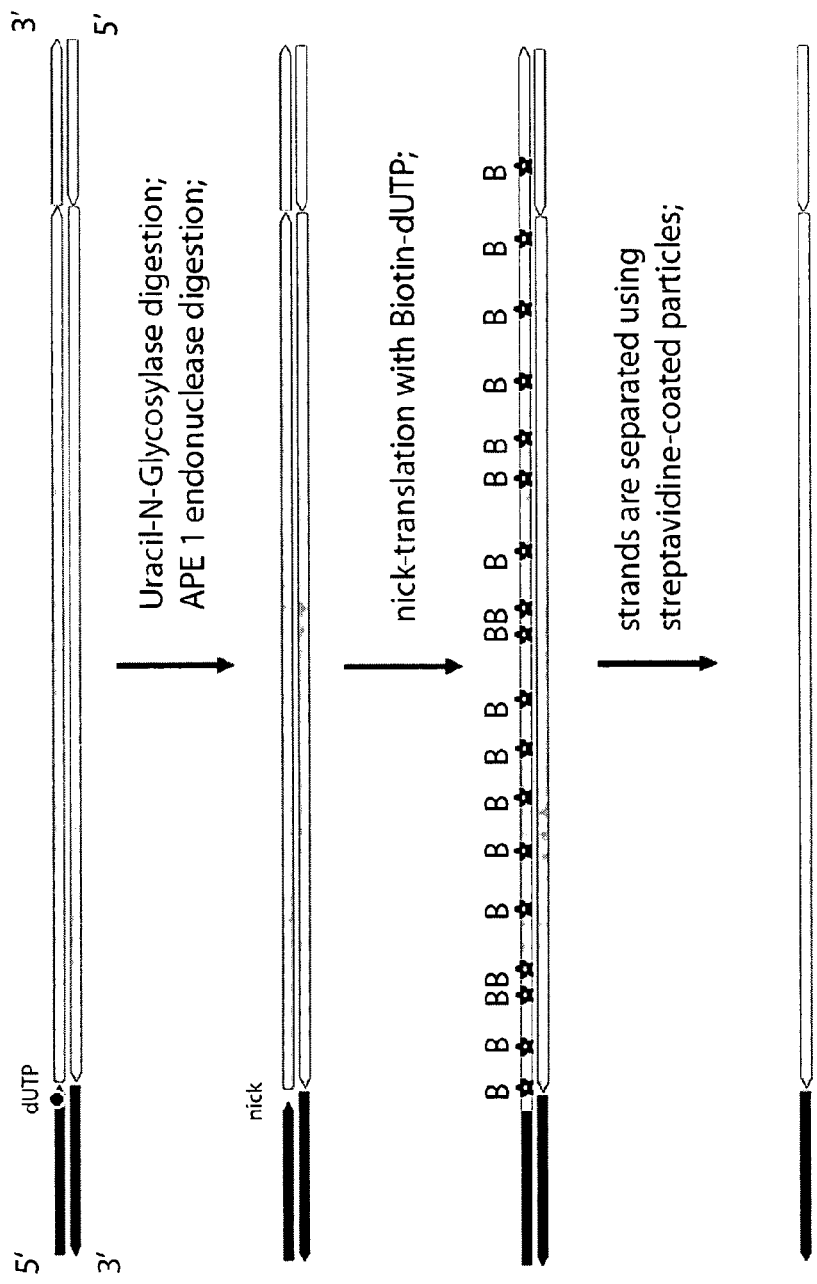
Figure 4:
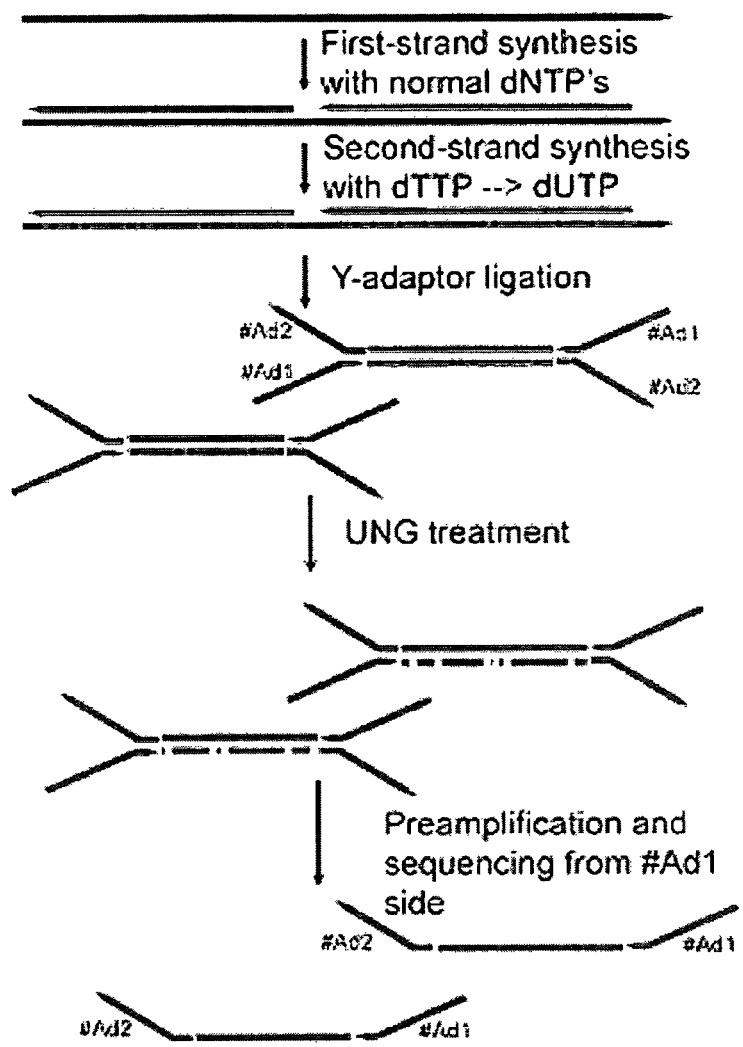

FIG. 3B: Preparation of single-stranded DNA according to the inventive method using biotinylated nucleotides the double-stranded DNA is a product of PCR reaction where one of the PCR-primers has dUTP at 3'-part;

dUTP in the PCR primer is converted into a nick: Uracil-N-Glycosylase converts dUTP into an abasic site and APE 1 nuclease converts the abasic site into a nick;

nick-translation is performed by DNA polymerase I (or Taq polymerase) in presence of biotin-associated dTTPs and/or biotin-associated dUTPs;

strands are separated using streptavidine-coated particles;

FIG. 4: Flowchart of the inventive method

RNA is shown in red colour, DNA in green. Arrows are in 5' to 3' direction.

Figure 5:
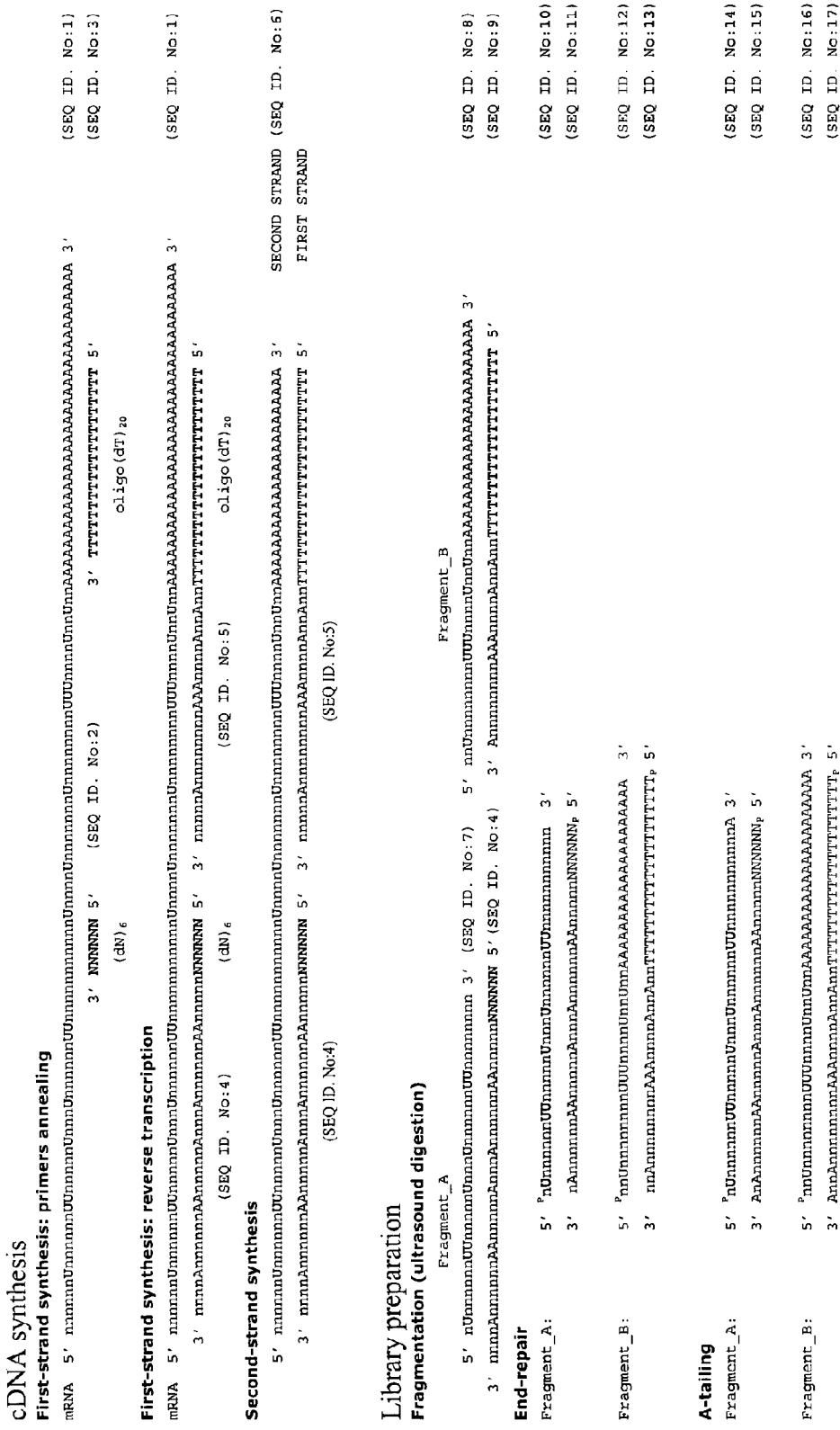

FIG. 5: Schematic view of the inventive method on the level of base pairs

FIG. 6: Expression profile of a yeast gene (A) A conventional transcriptional profile of the yeast YGR203W gene without orientation is shown. Vertical lines mark the boundaries of the YGR203W gene as they were determined previously (B) A transcriptional profile of the yeast YGR203W gene with orientation according to the inventive method is depicted. Reads mapped in the forward direction are shown in blue, in the reverse direction in red.

Figure 7:
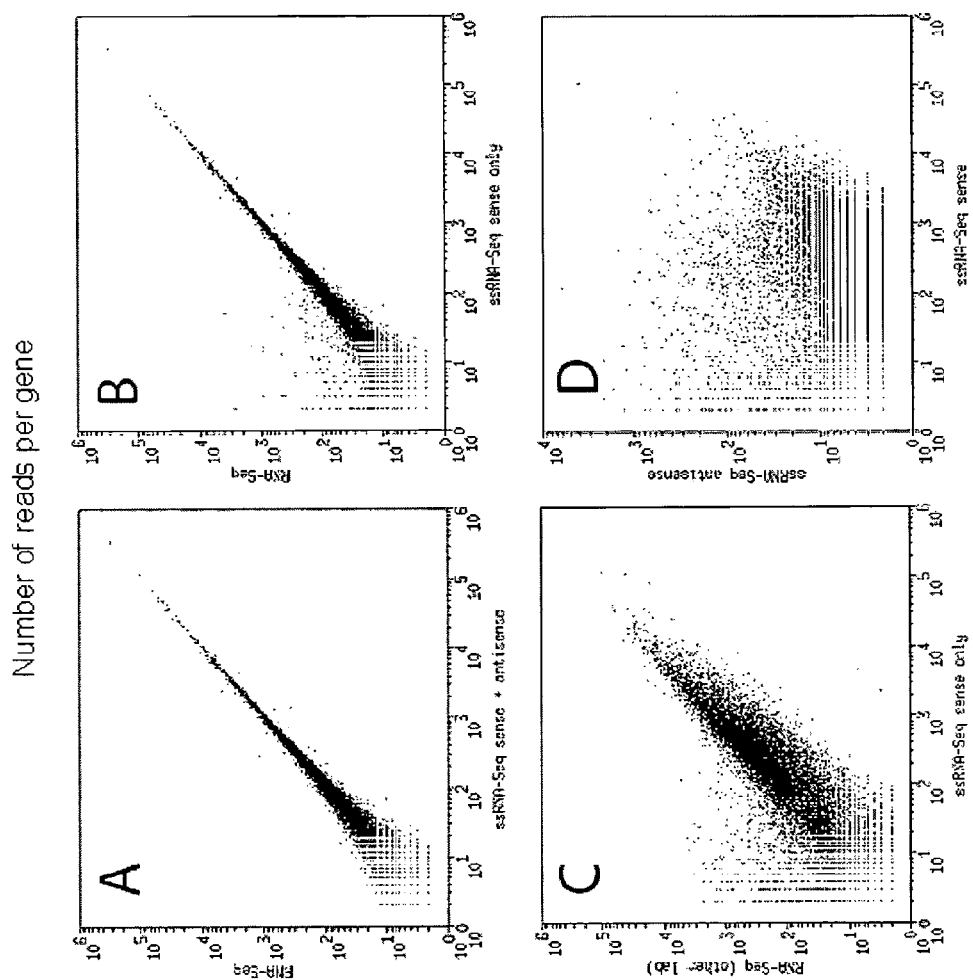

FIG. 7: Scatter plots comparing mouse mRNA expression data (number of reads in annotated genes)

(A) The same mouse liver sample, strand-specific (according to the method, X-axis) and strand-unspecific (RNA-Seq, Y-axis) protocols (Pearson correlation coefficient (cc)=0.999). A distribution close to unity would corresponds to a high correlation in these scatter plots.

(B) results according to the method for two biological replicas (mouse whole brain mRNA); cc=0.990.

(C) Mouse whole brain expression data according to the method (X-axis) and data from Mortazavi et al. 2008 (Y-axis); cc=0.817.

(D) Sense (X-axis) and antisense (Y-axis) expression in mouse brain. Thus the inventive method allows for a good differentiation of sense and antisense transcripts.

FIG. 8: Comparison of ssRNA-Seq results for protocols using 75%125% dUTP/dTTP mixture and 100% dUTP (A) Scatter plot of levels of sense transcription.

(B) Scatter plot of levels of antisense transcription.

Still a good correlation can be reached. Thus the inventive method does not depend on a complete exchange of at least one dNTP by a degradable analogue.

Figure 9:
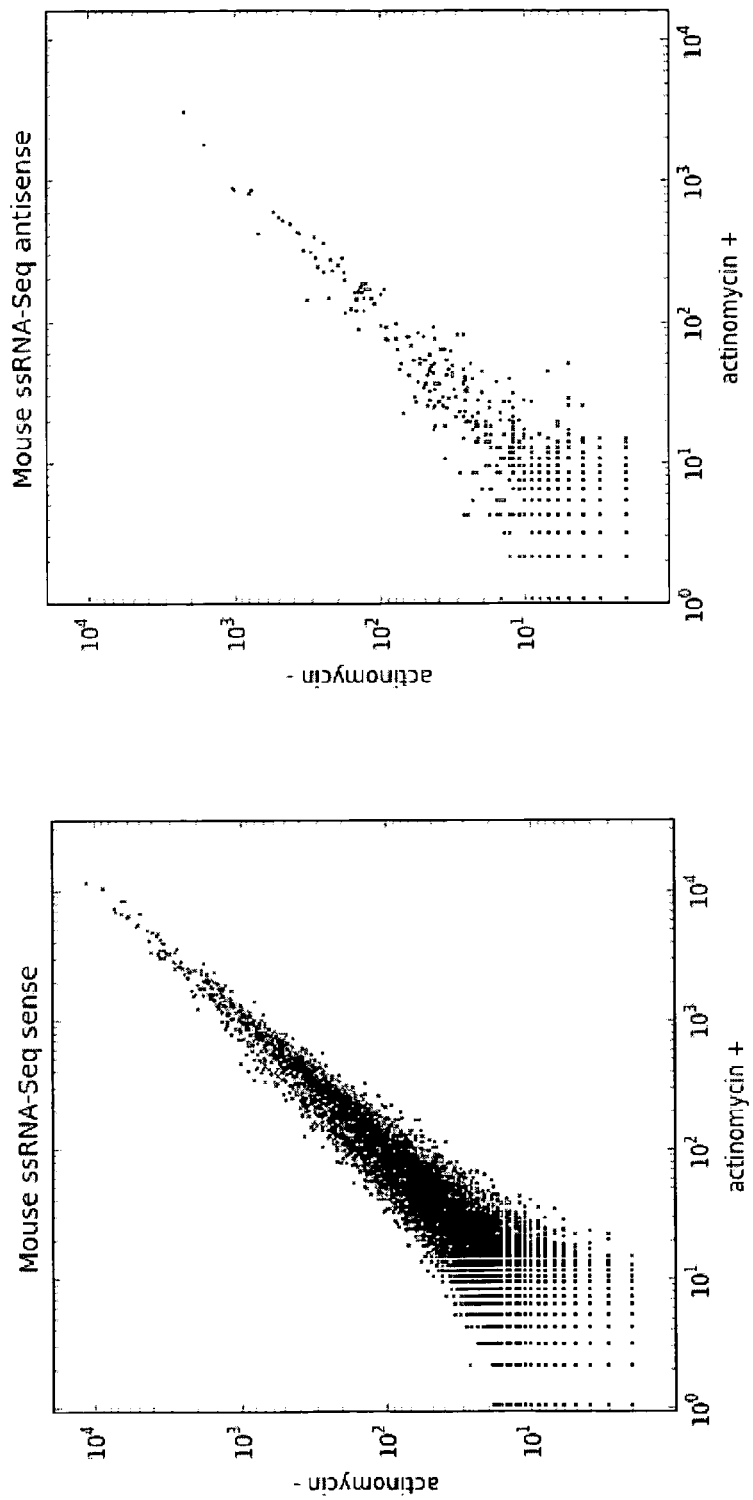

FIG. 9: Comparison of ssRNA-Seq results for protocols with and without actinomycin D added to the reverse transcription reaction (A) Scatter plot of levels of sense transcription.

(B) Scatter plot of levels of antisense transcription.

X-Axe: with actinomycin D; Y-Axe: without actinomycin D. The use of actinomycin D does not bias significantly the correlation when using sense strands.

FIG. 10: Examples of overlapping genes and novel gene-candidates

A. *S. cerevisiae* transcriptome. Overlapping tails of two genes:

B. *S. cerevisiae* transcriptome. Overlapping of three genes:

C. *S. cerevisiae* transcriptome. Novel gene-candidate between

D. Mouse whole brain transcriptome. Overlapping genes: Ncaph2 and Ecgf1.

E. Mouse whole brain transcriptome. genes: Mrpl24 and BC023814.

F. Mouse whole brain transcriptome. One unannotated and one incorrectly annotated exon of Cdc42bpa mouse gene.

G. Mouse whole brain transcriptome. Novel exon of Chd3 gene.

H. Mouse whole brain transcriptome. Novel gene-candidate.

ssRNA-Seq stands for single-strand RNA sequencing carried out according to the method.

EXAMPLES

Example 1

Transcriptome of *Saccharomyces cerevisiae*

In this example an application of the method according to the invention in a preferred embodiment is presented. Strand-specific sequencing of the yeast transcriptome is performed. Subsequently, the sequence of each clone is determined and matched with already existing DNA sequence of the yeast genome.

RNA Isolation:

Yeast strain BY4741 (MATa; his3Δ1; leu2Δ0; met15Δ0; ura3Δ0) was grown in rich medium (YPD; BD Company) at 30° C. overnight, diluted to an $OD_{600}$ of 0.15 and grown until reaching an $OD_{600}$ of 0.87. The cells were harvested by centrifugation at room temperature, washed once with 1×PBS, and frozen in liquid nitrogen. Total RNA was extracted using the RiboPure™-Yeast kit (Ambion) and analyzed by an Agilent 2100 bioanalyzer (Agilent Technologies).

polyA⁺ RNA Purification:

polyA⁺ RNA was purified with the Dynabeads mRNA purification kit (Invitrogen) following manufacturer's instructions and treated for 30 min at 37° C. with 0.2 u TURBO™ DNase (Ambion) per 1 µg of RNA.

First Strand Synthesis (FSS):

A typical FSS reaction was prepared by mixing 0.5 µg of polyA⁺ RNA, 40 ng of $(dN)_6$ primers (Invitrogen) and 25 pmol of oligo(dT) primer (Invitrogen) in 8.5 µl of 1× reverse transcription buffer (Invitrogen), 0.5 mM dNTP's, 5 mM $MgCl_2$ and 10 mM DTT. The mixture was incubated at 98° C. for 1 min to melt RNA secondary structures, then at 70° C. for 5 min and was ramped to 15° C. at 0.1° C./sec. Slow temperature ramp was used to make secondary structures of RNA and primers annealing as reproducible as possible. At 15° C. 0.5 µl of actinomycin D solution (120 ng/µl), 0.5 µl of RNase OUT (40 u/µl, Invitrogen) and 0.5 µl of Superscript III polymerase (200 u/µl, Invitrogen) were added to the reaction. Reverse transcription reaction temperature was increased gradually as a compromise between survival of the enzyme, stability of the primers and denaturation of RNA secondary structures: ramp from 15 to 25° C. at 0.1° C./sec; incubation at 25° C. for 10 min; ramp from 25 to 42° C. at 0.1° C./sec; incubation at 42° C. for 45 min; ramp from 42 to 50° C. at 0.1° C./sec; incubation at 50° C. for 25 min. Superscript III polymerase was finally inactivated at 75° C. for 15 min.

Removal of dNTPs:

20 μl of EB (10 mM TrisCl, pH 8.5, Qiagen) was added to the reaction. dNTPs were removed by purification of the first strand mixture on a self-made 200 μl G-50 gel-filtration spin-column equilibrated with 1 mM TrisCl, pH 7.0.

Second Strand Synthesis (SSS):

The Invitrogen kit for second strand synthesis was used. Therefore the first strand synthesis buffer was restored after gel-filtration column. It is possible to prepare self-made buffer and reduce the number of buffers. Water was added to the purified FSS reaction to bring the final volume to 52.5 μl. The mixture was cooled on ice. Then 22.5 μl of the "second strand mixture" (1 μl of 10× reverse transcription buffer (Invitrogen); 0.5 μl of 100 mM $MgCl_2$; 1 μl of 0.1 M DTT; 2 μl of 10 mM mixture of each: dATP, dGTP, dCTP, dUTP; 15 μl of 5×SSS buffer (Invitrogen); 0.5 μl of E. coli ligase (10 u/μl, NEB); 2 μl of DNA polymerase I (10 u/μl, NEB) and 0.5 μl RNase H (2 u/μl, Invitrogen)) were added. SSS reaction was incubated at 16° C. for 2 hours. ds cDNA was purified on QIAquick columns (Qiagen) according to the manufacturer's instructions.

DNA Fragmentation:

About 250 ng of double-stranded cDNA was fragmented by sonication on a UTR200 (Hielscher Ultrasonics GmbH, Germany) under the following conditions: 1 hour, 50% pulse, 100% power, and continuous cooling by 0° C. water flow-through.

Preparation of Libraries for Illumina Sequencing Platform:

Libraries were prepared using the DNA sample kit (#FC-102-1002, Illumina), as described in (Sultan et al. 2008), but with the following modifications: just before library amplification uridine digestion was performed at 37° C. for 15 min in 5 μl of 1×TE buffer, pH 7.5 with 1 u UNG (Applied Biosystems).

Procedure of paired-end sequencing library preparation was the same except that other ligation adapters and PCR primers were used (#PE-102-1002, Illumina).

Sequencing:

Amplified material was loaded onto flowcell at 4 pM concentration. Sequencing was carried out on the Illumina 1G Genome Analyser by running 36 cycles according to the manufacturer's instructions.

Data Analysis:

Images deconvolution, quality values calculation, mapping of exonic reads and exon junctions were performed as described in the art. Sequencing reads were aligned to S. cerevisiae (UCSC sacCer1) genomes using modification of Eland software (Gerald module v.1.27, Illumina). The mapping criteria of Eland are the following: sequencing read should be uniquely match to the genome allowing up to two mismatches, without insertions or deletions. The following recursive modification of Eland procedure was applied: first 32 bp of reads (trimming the last 4 bp of 36 bp reads due to Eland limitations) were aligned, then reads which do not match on reference by Eland criteria were trimmed to 31 bp, and aligned again. This 3'-end trimming of unmatched reads was done recursively down to 25 bp length. The modified procedure increases gain of uniquely aligned fragments typically by 20-50%, because the sequencing errors, which prevent successful alignment by Eland criteria, are located mostly on reads ends, which are gradually trimmed. Under these conditions, ~60% of the reads obtained here are matched to unique locations of the reference genome, whereas ~25% of the reads map to more than one genomic position and about 15% do not map.

Mapping End Tags:

Unmapped sequencing reads with 1-11 nt long leading oligo(dT) stretches were used for mapping of the 3'-gene boundaries. Leading oligo(dT) stretches were removed, and if the remaining fragment length was longer or equal to 25 bp, it was aligned on reference genome.

Search for Novel Genes:

The search for novel genes in yeast using RNA-Seq was previously performed. Such an algorithm was not used herein, since it was not accurately described in the art. To estimate roughly how the knowledge of RNA orientation influences the number of novel gene-candidates the following procedure was used. A search algorithm presented below gives 377 novel gene candidates without taking into account RNA orientation. It is about the same number as in the art. To use information about RNA orientation the search was performed twice (for reads mapped in the forward direction and then for reads mapped in the reverse direction), yielding in 549 novel gene candidates in forward orientation and 512—in reverse. The whole genome was split into 50 bp windows (non-sliding). A "new gene" was defined as a joined group of more than 2 consecutive windows, with at least 2 sequence reads (of the same direction) mapped per window. The gap between "new genes" should be at least 50 bp, the gap between "new gene" and an annotated gene (with the same transcription direction as the "new gene")—at least 100 bp.

With the RNA-Seq procedure it is possible to determine the 3'-boundaries of genes using those sequencing reads, which overlap with 3'-borders of genes. These reads may be mapped to the reference genome only after removal of oligo(dT) tail. The inventive method has the advantage of reduced noise in comparison with the RNA-Seq protocol because only one orientation of the homopolymeric stretch is allowed.

Example 2

Transcriptome of the Brain of Mus musculus

In this example a further application of the method according to the invention is presented. Strand-specific sequencing of the whole mouse brain transcriptome is performed. Subsequently, the sequence of each clone is determined and matched with already existing DNA sequence of the mouse genome. Methods are similar to those used in Example 1. Therefore only steps which differ from Example 1 are indicated.

RNA Isolation:

Two eleven weeks old female mice (C57B1/6J) were dissected and the whole brain was taken for RNA preparation. Total RNA was extracted using the Trizol method.

Data Analysis:

The resulting sequencing reads were aligned to the M. musculus (UCSC mm9) genomes using modification of Eland software (Gerald module v.1.27, Illumina).

Example 3

Comparison of Strand-Specific and Non-Strand-Specific Amplification of Polynucleotides To demonstrate that second-strand synthesis with deoxyuridine does not disturb the transcriptional landscape both strand-specific (according to the inventive method) and non-strand-specific transcriptome (RNA-Seq) sequencing for the same RNA sample was performed (mouse liver transcriptome). The resulting scatter plot (FIG. 7A) shows that both RNA-Seq and the inventive method produce identical transcription patterns.

Example 4

Reproducibiliity of the Inventive Method and Comparison with Previously Published Results from Another Laboratory In order to test the reproducibility of the inventive method independent analyses of whole brain mouse (FIG. 7B) transcriptomes were carried out under identical conditions. A high reproducibility can be seen in the respective scatter plots. A comparison of the data with previously published results also demonstrates good correlation (FIG. 7C).

Example 5

Stability of the Inventive Method

The inventive method results in a high degree of certainty in identifying transcript polarity. In theory, one uridine base in a molecule of a sequencing library is enough to prevent the appearance of a sequencing read from the false strand. Even if UNG occasionally does not remove the uridine base, the molecule still would not be amplified, since uridine-containing template strongly suppresses Phusion DNA polymerase used for library amplification. Apparently, most second cDNA strands in the library contain more than one uridine base, because a 75%125% dUTP/dTTP mixture in the second strand synthesis reaction gives essentially the same results as 100% dUTP (FIGS. 8A and 8B).

Example 6

Influence of Actinomycin D

To prevent spurious second-strand cDNA synthesis, which was shown to be the major source of artifactual antisense transcripts. Antisense artifacts in transcriptome microarray experiments are resolved by actinomycin D. Actinomycin D was included in the reverse transcription reaction. Actinomycin D specifically inhibits DNA-dependent, but not RNA-dependent, DNA synthesis. The presence of actinomycin D in the reaction practically did not influence the level of antisense transcription (FIGS. 9A and 9B). Actinomycin D is included in the protocol to make the reaction more reproducible.

Example 7

Transcriptome of the Liver of *Mus musculus*

In this example a further application of the method according to the invention is presented. Strand-specific sequencing of the whole mouse liver transcriptome is performed. Subsequently, the sequence of each clone is determined and matched with already existing DNA sequence of the mouse genome. Methods are similar to those used in Example 1. Therefore only steps which differ from Example 1 are indicated.
ds cDNA Synthesis:
  dTTP was substituted by dUTP during first strand cDNA synthesis. For the second strand cDNA synthesis, the mixture of standard dNTPs was used.
Data Analysis:
  The resulting sequencing reads were aligned to the *M. musculus* (UCSC mm9) genomes using modification of Eland software (Gerald module v.1.27, Illumina).

Example 8

Transcriptome of the Human Samples from Blood and Tumor (Melanoma)

In this example a further application of the method according to the invention is presented. Strand-specific sequencing of the human transcriptome is performed. Subsequently, the sequence of each clone is determined and matched with already existing DNA sequence of the human genome (hg18, NCBI build 36.1). Methods are similar to those used in Example 1. Therefore only steps which differ from Example 1 are indicated.
ds cDNA Preparation:
  Poly A RNA was chemically fragmented prior to ds cDNA synthesis. Compared to ultrasound shearing after ds cDNA synthesis this approach resulted in a more even distribution of reads along the transcript (no 3' bias).

Example 9

Transcriptome of *E. coli*

In this example a further application of the method according to the invention is presented. Strand-specific sequencing of the *E. coli* transcriptome is performed. Subsequently, the sequence of each clone is determined and matched with already existing DNA sequence of the *E. coli* (K12 reference genome (NC_000913). Methods are similar to those used in Example 1. Therefore only steps which differ from Example 1 are indicated.
ds cDNA Preparation:
  Instead of dUTP, biotinylated dTTP was used for the second strand cDNA synthesis.
Sequencing Library Preparation.
  After ligation of polarity-specific Y-shaped adapters, biotinylated strand was separated from non-biotinylated using streptavidine coated magnetic beads. Biotinylated strand was further used for amplification.
Data Analysis:
  The resulting sequencing reads were aligned to K12 reference genome (NC_000913) using the Eland program (Gerald module v.1.27 of the Illumina pipeline)).

Example 10

Preparation of Single-Stranded Hybridisation Target

The task was to prepare an array with spotted single-stranded molecules, corresponding to different genomic regions (300-500 bp long). First, selected regions were amplified using genomic DNA as a template and PCR primers corresponding to the genomic DNA, where one primer in each pair was selected so, that it had at least one T within last 3 nucleotides on the 3' end of the primer. This dTTP was substituted by dUTP during the primer synthesis. Usage of such uridine-containing primer in PCR resulted in obtaining PCR product with an uridine-marked strand.

PCR products were purified. After UNG treatment and APE 1 digestion a nick appeared in the uridine-containing strand in the place of uridine. From that nick, a nick-translation reaction was performed using dNTP mix with dUTP instead of dTTP and DNA polymerase I in a corresponding buffer. Nick-translation resulted in substitution of one of the strands in a PCR product to a strand containing multiple UTPs along its whole length (FIG. 3A). After UNG treatment and heating, the uridine strand was destroyed. Resulting small fragments were washed off by purification on a silica column. Single stranded DNA molecules were spotted on Nexterion slides (Schott) according to the manufacturers instructions.

Example 11

Preparation of Single-Stranded Hybridisation Target

The task and methods were similar to those used in Example 10. The difference was that biotin-associated dTTP were used instead of dUTP in the nick-translation reaction. Biotinylated strand was further separated from non-biotinylated by immobilisation on streptavidine-coated magnetic beads. The non-biotinylated strand was further used for hybridization.

The invention claimed is:

1. A method for preparing a nucleic acid molecule for strand-specific sequencing, comprising:
 (a) producing a double-stranded DNA by:
  (i) reverse transcribing an RNA to make a first DNA strand; and
  (ii) copying the first DNA strand in the presence of a dUTP to make a second DNA strand comprising one or more deoxyuridines;
 (b) amplifying, by PCR, at least part of the first DNA strand but not the second DNA strand of the double-stranded DNA by:
  (i) subjecting the product of step (a) or a fragment thereof to amplification using a polymerase that is suppressed by a template comprising deoxyuridine; and/or
  (ii) treating the product of step (a) or a fragment thereof with uracil-N-glycosylase (UDG) to remove uracil from the second strand and then amplifying the UDG-treated product using a polymerase.

2. The method of claim 1, wherein the RNA of step (a)(i) is produced by fragmenting an initial RNA sample.

3. The method of claim 1, wherein the method comprises fragmenting the double-stranded DNA of step (a) to produce DNA fragments, prior to step (b).

4. The method of claim 3, wherein the fragmenting comprises sonicating or enzymatically digesting the double-stranded DNA.

5. The method of claim 1, wherein the method further comprises at step (a) ligating adaptors to the double-stranded DNA, or a fragment thereof, prior to step (b).

6. The method of claim 5, wherein the ligating comprises attaching different adaptor sequences to the 5' and 3' ends of the first DNA strand in the double-stranded DNA or fragment thereof.

7. The method of claim 6, wherein the method comprises ligating a Y adaptor to the double-stranded DNA, or a fragments thereof, prior to step (b).

8. The method of claim 1, wherein the reverse transcribing step (a)(i) is done using an olgo(dT) primer or a random primer.

9. The method of claim 1, wherein the reverse transcribing step (a)(i) is done using a reverse transcriptase selected from the group consisting of: human immune deficiency virus 1 reverse transcriptase, Moloney murine leukemia virus reverse transcriptase, avian myeloblastosis virus reverse transcriptase, telomerase reverse transcriptase, or a functional variant thereof.

10. The method of claim 1, wherein the copying step (a)(ii) is done in the presence of a dUTP and RNaseH to make a second DNA strand comprising one or more deoxyuridines.

11. The method of claim 1, wherein the method comprises:
 (a) producing the double-stranded DNA by:
  (i) reverse transcribing an RNA to make a first DNA strand;
  (ii) copying the first DNA strand in the presence of a dUTP and RNaseH to make a second DNA strand comprising one or more deoxyuridines;
  (iii) fragmenting the product of step (ii) by sonication to produce fragments;
  (iv) end-polishing the fragments; and
  (v) ligating adaptors to the end-polished fragments;
 (b) amplifying, by PCR, at least part of the first DNA strand but not the second DNA strand of the double-stranded DNA by:
  (i) treating the product of step (a) with uracil-N-glycosylase (UDG) to remove uracil from the second strand;
  (ii) heating the UDG-treated DNA to degrade the second DNA strand; and
  (iii) amplifying the first DNA strand using a polymerase and one or more primers that hybridize to the adaptors added in (a)(v).

12. The method of claim 1, wherein the method comprises:
 (a) producing a double-stranded DNA by:
  (i) fragmenting an initial RNA sample;
  (ii) reverse transcribing the fragmented RNA to make a first DNA strand;
  (iii) copying the first DNA strand in the presence of a dUTP to make a second DNA strand comprising one or more deoxyuridines;
  (iv) A-tailing the product of step (iii); and
  (v) ligating an adaptor to the A-tailed product of (iv);
 (b) amplifying, by PCR, at least part of the first DNA strand but not the second DNA strand of the double-stranded DNA by subjecting the product of step (a) to amplification using a polymerase that is suppressed by a template comprising deoxyuridine and one or more primers that hybridize to the adaptor added in (a)(v).

13. The method of claim 1, wherein the method comprises:
 (a) producing a double-stranded DNA by:
  (i) fragmenting an initial RNA sample;
  (ii) reverse transcribing the fragmented RNA to make a first DNA strand;
  (iii) copying the first DNA strand in the presence of a dUTP to make a second DNA strand comprising one or more deoxyuridines;
  (iv) A-tailing the product of step (iii); and
  (v) ligating adaptors to the A-tailed product of (iv);
 (b) amplifying, by PCR, at least part of the first DNA strand but not the second DNA strand of the double-stranded DNA by treating the product of step (a) with uracil-N-glycosylase (UDG) to remove uracil from the second strand and then amplifying the UDG-treated product using a polymerase and one or more primers that hybridize to the adaptor added in (a)(v).

* * * * *

SEQUENCE LISTING

```
<160> NUMBER OF SEQ ID NOS: 39

<210> SEQ ID NO 1
<211> LENGTH: 113
<212> TYPE: RNA
<213> ORGANISM: Artificial Sequence
<220> FEATURE:
<223> OTHER INFORMATION: synthetic polynucleotide sequence
<220> FEATURE:
<221> NAME/KEY: misc_feature
<222> LOCATION: (1)..(6)
<223> OTHER INFORMATION: n is a, c, g, or u
<220> FEATURE:
<221> NAME/KEY: misc_feature
<222> LOCATION: (8)..(13)
<223> OTHER INFORMATION: n is a, c, g, or u
<220> FEATURE:
<221> NAME/KEY: misc_feature
<222> LOCATION: (16)..(20)
<223> OTHER INFORMATION: n is a, c, g, or u
<220> FEATURE:
<221> NAME/KEY: misc_feature
<222> LOCATION: (22)..(24)
<223> OTHER INFORMATION: n is a, c, g, or u
<220> FEATURE:
<221> NAME/KEY: misc_feature
<222> LOCATION: (26)..(31)
<223> OTHER INFORMATION: n is a, c, g, or u
<220> FEATURE:
<221> NAME/KEY: misc_feature
<222> LOCATION: (34)..(44)
<223> OTHER INFORMATION: n is a, c, g, or u
<220> FEATURE:
<221> NAME/KEY: misc_feature
<222> LOCATION: (46)..(49)
<223> OTHER INFORMATION: n is a, c, g, or u
<220> FEATURE:
<221> NAME/KEY: misc_feature
<222> LOCATION: (51)..(57)
<223> OTHER INFORMATION: n is a, c, g, or u
<220> FEATURE:
<221> NAME/KEY: misc_feature
<222> LOCATION: (59)..(66)
<223> OTHER INFORMATION: n is a, c, g, or u
<220> FEATURE:
<221> NAME/KEY: misc_feature
<222> LOCATION: (70)..(73)
<223> OTHER INFORMATION: n is a, c, g, or u
<220> FEATURE:
<221> NAME/KEY: misc_feature
<222> LOCATION: (75)..(76)
<223> OTHER INFORMATION: n is a, c, g, or u
<220> FEATURE:
<221> NAME/KEY: misc_feature
<222> LOCATION: (78)..(79)
<223> OTHER INFORMATION: n is a, c, g, or u

<400> SEQUENCE: 1
nnnnnnunnn nnnuunnnnn unnnunnnnn nuunnnnnnn nnnnunnnnu nnnnnnnunn      60
nnnnnnuuun nnnunnunna aaaaaaaaaa aaaaaaaaaa aaaaaaaaaa aaa            113
```

-continued

<210> SEQ ID NO 2
<211> LENGTH: 6
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(6)
<223> OTHER INFORMATION: n is a, c, g, or t

<400> SEQUENCE: 2 nnnnnn                                                                  6

<210> SEQ ID NO 3
<211> LENGTH: 20
<212> TYPE: DNA
<213> ORGANISM: Artificial sequence
<220> FEATURE:
<223> OTHER INFORMATION: synthetic polynucleotide sequence

<400> SEQUENCE: 3
tttttttttt tttttttttt                                                  20

<210> SEQ ID NO 4
<211> LENGTH: 42
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (25)..(29)
<223> OTHER INFORMATION: n is a, c, g, or t
<220> FEATURE:
<221> NAME/KEY: misc_feature
<222> LOCATION: (32)..(37)
<223> OTHER INFORMATION: n is a, c, g, or t
<220> FEATURE:
<221> NAME/KEY: misc_feature
<222> LOCATION: (39)..(42)
<223> OTHER INFORMATION: n is a, c, g, or t

<400> SEQUENCE: 4
nnnnnnnnnn naannnnnna nnnannnnna annnnnnann nn                         42

<210> SEQ ID NO 5
<211> LENGTH: 50
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)

```
<223> OTHER INFORMATION: n is a, c, g, or t
<220> FEATURE:
<221> NAME/KEY: misc_feature
<222> LOCATION: (30)..(33)
<223> OTHER INFORMATION: n is a, c, g, or t
<220> FEATURE:
<221> NAME/KEY: misc_feature
<222> LOCATION: (37)..(44)
<223> OTHER INFORMATION: n is a, c, g, or t
<220> FEATURE:
<221> NAME/KEY: misc_feature
<222> LOCATION: (46)..(50)
<223> OTHER INFORMATION: n is a, c, g, or t

<400> SEQUENCE: 5
tttttttttt tttttttttt tttnnannan nnnaaannnn nnnnannnnn                  50

<210> SEQ ID NO 6
<211> LENGTH: 102
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(6)
<223> OTHER INFORMATION: n is a, c, g, t or u
<220> FEATURE:
<221> NAME/KEY: misc_feature
<222> LOCATION: (8)..(13)
<223> OTHER INFORMATION: n is a, c, g, t or u
<220> FEATURE:
<221> NAME/KEY: misc_feature
<222> LOCATION: (16)..(20)
<223> OTHER INFORMATION: n is a, c, g, t or u
<220> FEATURE:
<221> NAME/KEY: misc_feature
<222> LOCATION: (22)..(24)
<223> OTHER INFORMATION: n is a, c, g, t or u
<220> FEATURE:
<221> NAME/KEY: misc_feature
<222> LOCATION: (26)..(31)
<223> OTHER INFORMATION: n is a, c, g, t or u
<220> FEATURE:
<221> NAME/KEY: misc_feature
<222> LOCATION: (34)..(44)
<223> OTHER INFORMATION: n is a, c, g, t or u
<220> FEATURE:
<221> NAME/KEY: misc_feature
<222> LOCATION: (46)..(49)
<223> OTHER INFORMATION: n is a, c, g, t or u
<220> FEATURE:
<221> NAME/KEY: misc_feature
<222> LOCATION: (51)..(57)
<223> OTHER INFORMATION: n is a, c, g, t or u
<220> FEATURE:
<221> NAME/KEY: misc_feature
<222> LOCATION: (59)..(66)
<223> OTHER INFORMATION: n is a, c, g, t or u
<220> FEATURE:
<221> NAME/KEY: misc_feature
<222> LOCATION: (70)..(73)
<223> OTHER INFORMATION: n is a, c, g, t or u
<220> FEATURE:
<221> NAME/KEY: misc_feature
<222> LOCATION: (75)..(76)
<223> OTHER INFORMATION: n is a, c, g, t or u
<220> FEATURE:
<221> NAME/KEY: misc_feature
<222> LOCATION: (78)..(79)
<223> OTHER INFORMATION: n is a, c, g, t or u

<400> SEQUENCE: 6
nnnnnnunnn nnnuunnnnn unnnunnnnn nuunnnnnnn nnnnunnnnu nnnnnnnnunn       60 nnnnnnuuun nnnunnunna aaaaaaaaaa aaaaaaaaaa aa                          102
```

<210> SEQ ID NO 7
<211> LENGTH: 36
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(8)
<223> OTHER INFORMATION: n is a, c, g, t or u
<220> FEATURE:
<221> NAME/KEY: misc_feature
<222> LOCATION: (11)..(15)
<223> OTHER INFORMATION: n is a, c, g, t or u
<220> FEATURE:
<221> NAME/KEY: misc_feature
<222> LOCATION: (17)..(19)
<223> OTHER INFORMATION: n is a, c, g, t or u
<220> FEATURE:
<221> NAME/KEY: misc_feature
<222> LOCATION: (21)..(26)
<223> OTHER INFORMATION: n is a, c, g, t or u
<220> FEATURE:
<221> NAME/KEY: misc_feature
<222> LOCATION: (29)..(36)
<223> OTHER INFORMATION: n is a, c, g, t or u

<400> SEQUENCE: 7
nunnnnnnuu nnnnnunnnu nnnnnnuunn nnnnnn        36

<210> SEQ ID NO 8
<211> LENGTH: 47
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: misc_feature
<222> LOCATION: (4)..(11)
<223> OTHER INFORMATION: n is a, c, g, t or u
<220> FEATURE:
<221> NAME/KEY: misc_feature
<222> LOCATION: (15)..(18)
<223> OTHER INFORMATION: n is a, c, g, t or u
<220> FEATURE:
<221> NAME/KEY: misc_feature
<222> LOCATION: (20)..(21)
<223> OTHER INFORMATION: n is a, c, g, t or u
<220> FEATURE:
<221> NAME/KEY: misc_feature
<222> LOCATION: (23)..(24)
<223> OTHER INFORMATION: n is a, c, g, t or u

<400> SEQUENCE: 8
nnunnnnnnn nuunnnnun nunnaaaaaa aaaaaaaaa aaaaaaa        47

<210> SEQ ID NO 9
<211> LENGTH: 42
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (21)..(22)

```
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (34)..(41)
<223> OTHER INFORMATION: n is a, c, g, or t

<400> SEQUENCE: 9
tttttttttt tttttttttt nnannannnn aaannnnnnn na                              42

<210> SEQ ID NO 10
<211> LENGTH: 39
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(8)
<223> OTHER INFORMATION: n is a, c, g, t or u
<220> FEATURE:
<221> NAME/KEY: misc_feature
<222> LOCATION: (11)..(15)
<223> OTHER INFORMATION: n is a, c, g, t or u
<220> FEATURE:
<221> NAME/KEY: misc_feature
<222> LOCATION: (17)..(19)
<223> OTHER INFORMATION: n is a, c, g, t or u
<220> FEATURE:
<221> NAME/KEY: misc_feature
<222> LOCATION: (21)..(26)
<223> OTHER INFORMATION: n is a, c, g, t or u
<220> FEATURE:
<221> NAME/KEY: misc_feature
<222> LOCATION: (29)..(39)
<223> OTHER INFORMATION: n is a, c, g, t or u

<400> SEQUENCE: 10
nunnnnnnuu nnnnnunnnu nnnnnnuunn nnnnnnnnn                                  39

<210> SEQ ID NO 11
<211> LENGTH: 39
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (25)..(29)
<223> OTHER INFORMATION: n is a, c, g, or t
<220> FEATURE:
<221> NAME/KEY: misc_feature
```

```
<222> LOCATION: (32)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 11
nnnnnnnnnn naannnnnna nnnannnnna annnnnnan                                  39

<210> SEQ ID NO 12
<211> LENGTH: 44
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(2)
<223> OTHER INFORMATION: n is a, c, g, t or u
<220> FEATURE:
<221> NAME/KEY: misc_feature
<222> LOCATION: (4)..(11)
<223> OTHER INFORMATION: n is a, c, g, t or u
<220> FEATURE:
<221> NAME/KEY: misc_feature
<222> LOCATION: (15)..(18)
<223> OTHER INFORMATION: n is a, c, g, t or u
<220> FEATURE:
<221> NAME/KEY: misc_feature
<222> LOCATION: (20)..(21)
<223> OTHER INFORMATION: n is a, c, g, t or u
<220> FEATURE:
<221> NAME/KEY: misc_feature
<222> LOCATION: (23)..(24)
<223> OTHER INFORMATION: n is a, c, g, t or u

<400> SEQUENCE: 12
nnunnnnnnn nuuunnnnun nunnaaaaaa aaaaaaaaaa aaaa                            44

<210> SEQ ID NO 13
<211> LENGTH: 44
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 13
tttttttttt tttttttttt nnannannnn aaannnnnnn nann                            44

<210> SEQ ID NO 14
<211> LENGTH: 40
<212> TYPE: DNA
```

```
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (3)..(8)
<223> OTHER INFORMATION: n is a, c, g, t or u
<220> FEATURE:
<221> NAME/KEY: misc_feature
<222> LOCATION: (11)..(15)
<223> OTHER INFORMATION: n is a, c, g, t or u
<220> FEATURE:
<221> NAME/KEY: misc_feature
<222> LOCATION: (17)..(19)
<223> OTHER INFORMATION: n is a, c, g, t or u
<220> FEATURE:
<221> NAME/KEY: misc_feature
<222> LOCATION: (21)..(26)
<223> OTHER INFORMATION: n is a, c, g, t or u
<220> FEATURE:
<221> NAME/KEY: misc_feature
<222> LOCATION: (29)..(39)
<223> OTHER INFORMATION: n is a, c, g, t or u

<400> SEQUENCE: 14
nunnnnnnuu nnnnnunnnu nnnnnnuunn nnnnnnnnna                                40

<210> SEQ ID NO 15
<211> LENGTH: 40
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (25)..(29)
<223> OTHER INFORMATION: n is a, c, g, or t
<220> FEATURE:
<221> NAME/KEY: misc_feature
<222> LOCATION: (32)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 15
nnnnnnnnnn naannnnnna nnnannnnna annnnnnana                                40

<210> SEQ ID NO 16
<211> LENGTH: 45
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(2)
<223> OTHER INFORMATION: n is a, c, g, t or u
```

```
<220> FEATURE:
<221> NAME/KEY: misc_feature
<222> LOCATION: (4)..(11)
<223> OTHER INFORMATION: n is a, c, g, t or u
<220> FEATURE:
<221> NAME/KEY: misc_feature
<222> LOCATION: (15)..(18)
<223> OTHER INFORMATION: n is a, c, g, t or u
<220> FEATURE:
<221> NAME/KEY: misc_feature
<222> LOCATION: (20)..(21)
<223> OTHER INFORMATION: n is a, c, g, t or u
<220> FEATURE:
<221> NAME/KEY: misc_feature
<222> LOCATION: (23)..(24)
<223> OTHER INFORMATION: n is a, c, g, t or u

<400> SEQUENCE: 16
nnunnnnnnn nuuunnnnun nunnaaaaaa aaaaaaaaaa aaaaa                    45

<210> SEQ ID NO 17
<211> LENGTH: 45
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (34)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 17
tttttttttt tttttttttt nnannannnn aaannnnnnn nanna                    45

<210> SEQ ID NO 18
<211> LENGTH: 107
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (35)..(35)
<223> OTHER INFORMATION: n is a, c, g, t or u
<220> FEATURE:
<221> NAME/KEY: misc_feature
<222> LOCATION: (37)..(42)
<223> OTHER INFORMATION: n is a, c, g, t or u
<220> FEATURE:
<221> NAME/KEY: misc_feature
<222> LOCATION: (45)..(49)
<223> OTHER INFORMATION: n is a, c, g, t or u
<220> FEATURE:
<221> NAME/KEY: misc_feature
<222> LOCATION: (51)..(53)
<223> OTHER INFORMATION: n is a, c, g, t or u
<220> FEATURE:
<221> NAME/KEY: misc_feature
<222> LOCATION: (55)..(60)
```

<223> OTHER INFORMATION: n is a, c, g, t or u
<220> FEATURE:
<221> NAME/KEY: misc_feature
<222> LOCATION: (63)..(68)
<223> OTHER INFORMATION: n is a, c, g, t or u
<220> FEATURE:
<221> NAME/KEY: misc_feature
<222> LOCATION: (70)..(73)
<223> OTHER INFORMATION: n is a, c, g, t or u

<400> SEQUENCE: 18
tacactcttt ccctacacga cgctcttccg atctnunnnn nnuunnnnnu nnnunnnnnn      60
uunnnnnnun nnnagatcgg aagagctcgt atgccgtctt ctgcttg                  107

<210> SEQ ID NO 19
<211> LENGTH: 107
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (35)..(45)
<223> OTHER INFORMATION: n is a, c, g, or t
<220> FEATURE:
<221> NAME/KEY: misc_feature
<222> LOCATION: (48)..(53)
<223> OTHER INFORMATION: n is a, c, g, or t
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (59)..(63)
<223> OTHER INFORMATION: n is a, c, g, or t
<220> FEATURE:
<221> NAME/KEY: misc_feature
<222> LOCATION: (66)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t

<400> SEQUENCE: 19
tacactcttt ccctacacga cgctcttccg atctnnnnnn nnnnnaannn nnnannnann      60
nnnaannnnn nanagatcgg aagagctcgt atgccgtctt ctgcttg                  107

<210> SEQ ID NO 20
<211> LENGTH: 112
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (35)..(36)
<223> OTHER INFORMATION: n is a, c, g, t or u
<220> FEATURE:
<221> NAME/KEY: misc_feature
<222> LOCATION: (38)..(45)
<223> OTHER INFORMATION: n is a, c, g, t or u
<220> FEATURE:
<221> NAME/KEY: misc_feature
<222> LOCATION: (49)..(52)
<223> OTHER INFORMATION: n is a, c, g, t or u
<220> FEATURE:
<221> NAME/KEY: misc_feature
<222> LOCATION: (54)..(55)
<223> OTHER INFORMATION: n is a, c, g, t or u
<220> FEATURE:
<221> NAME/KEY: misc_feature

```
<222> LOCATION: (57)..(58)
<223> OTHER INFORMATION: n is a, c, g, t or u

<400> SEQUENCE: 20
tacactcttt ccctacacga cgctcttccg atctnnunnn nnnnnuuunn nnunnunnaa    60
aaaaaaaaaa aaaaaaaaag atcggaagag ctcgtatgcc gtcttctgct tg          112

<210> SEQ ID NO 21
<211> LENGTH: 112
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(64)
<223> OTHER INFORMATION: n is a, c, g, or t
<220> FEATURE:
<221> NAME/KEY: misc_feature
<222> LOCATION: (68)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t

<400> SEQUENCE: 21
tacactcttt ccctacacga cgctcttccg atctttttttt tttttttttt ttttnnanna    60
nnnnaaannn nnnnnannag atcggaagag ctcgtatgcc gtcttctgct tg          112

<210> SEQ ID NO 22
<211> LENGTH: 13
<212> TYPE: DNA
<213> ORGANISM: Artificial sequence
<220> FEATURE:
<223> OTHER INFORMATION: synthetic polynucleotide sequence

<400> SEQUENCE: 22
gctcttccga tct                                                      13

<210> SEQ ID NO 23
<211> LENGTH: 6
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(6)
<223> OTHER INFORMATION: n is a, c, g, or t

<400> SEQUENCE: 23 nnnnnn                                                               6

<210> SEQ ID NO 24
<211> LENGTH: 5
<212> TYPE: DNA
<213> ORGANISM: Artificial sequence
<220> FEATURE:
<223> OTHER INFORMATION: synthetic polynucleotide sequence
<220> FEATURE:
```

```
<221> NAME/KEY: misc_feature
<222> LOCATION: (1)..(5)
<223> OTHER INFORMATION: n is a, c, g, or t

<400> SEQUENCE: 24 nnnnn                                                                    5

<210> SEQ ID NO 25
<211> LENGTH: 3
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(3)
<223> OTHER INFORMATION: n is a, c, g, or t

<400> SEQUENCE: 25 nnn                                                                      3

<210> SEQ ID NO 26
<211> LENGTH: 6
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(6)
<223> OTHER INFORMATION: n is a, c, g, or t

<400> SEQUENCE: 26 nnnnnn                                                                   6

<210> SEQ ID NO 27
<211> LENGTH: 12
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(11)
<223> OTHER INFORMATION: n is a, c, g, or t

<400> SEQUENCE: 27
nnnnnnnnnn na                                                           12

<210> SEQ ID NO 28
<211> LENGTH: 13
<212> TYPE: DNA
<213> ORGANISM: Artificial sequence
<220> FEATURE:
<223> OTHER INFORMATION: synthetic polynucleotide sequence

<400> SEQUENCE: 28
gctcttccga tct                                                          13

<210> SEQ ID NO 29
<211> LENGTH: 8
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(8)
<223> OTHER INFORMATION: n is a, c, g, or t
```

```
<400> SEQUENCE: 29 nnnnnnnn                                                              8

<210> SEQ ID NO 30
<211> LENGTH: 4
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(4)
<223> OTHER INFORMATION: n is a, c, g, or t

<400> SEQUENCE: 30 nnnn                                                                  4

<210> SEQ ID NO 31
<211> LENGTH: 2
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(2)
<223> OTHER INFORMATION: n is a, c, g, or t

<400> SEQUENCE: 31 nn                                                                    2

<210> SEQ ID NO 32
<211> LENGTH: 23
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (1)..(2)
<223> OTHER INFORMATION: n is a, c, g, or t

<400> SEQUENCE: 32
nnaaaaaaaa aaaaaaaaaa aaa                                            23

<210> SEQ ID NO 33
<211> LENGTH: 34
<212> TYPE: DNA
<213> ORGANISM: Artificial sequence
<220> FEATURE:
<223> OTHER INFORMATION: synthetic polynucleotide sequence

<400> SEQUENCE: 33
caagcagaag acggcatacg agctcttccg atct                                34

<210> SEQ ID NO 34
<211> LENGTH: 58
<212> TYPE: DNA
<213> ORGANISM: Artificial sequence
<220> FEATURE:
<223> OTHER INFORMATION: synthetic polynucleotide sequence

<400> SEQUENCE: 34
aatgatacgg cgaccaccga gatctacact ctttccctac acgacgctct tccgatct      58

<210> SEQ ID NO 35
```

```
<211> LENGTH: 130
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (37)..(42)
<223> OTHER INFORMATION: n is a, c, g, or t
<220> FEATURE:
<221> NAME/KEY: misc_feature
<222> LOCATION: (45)..(49)
<223> OTHER INFORMATION: n is a, c, g, or t
<220> FEATURE:
<221> NAME/KEY: misc_feature
<222> LOCATION: (51)..(53)
<223> OTHER INFORMATION: n is a, c, g, or t
<220> FEATURE:
<221> NAME/KEY: misc_feature
<222> LOCATION: (55)..(60)
<223> OTHER INFORMATION: n is a, c, g, or t
<220> FEATURE:
<221> NAME/KEY: misc_feature
<222> LOCATION: (63)..(73)
<223> OTHER INFORMATION: n is a, c, g, or t

<400> SEQUENCE: 35
caagcagaag acggcatacg agctcttccg atctntnnnn nnttnnnnnt nnntnnnnnn      60
ttnnnnnnnn nnnagatcgg aagagcgtcg tgtagggaaa gagtgtagat ctcggtggtc     120
gccgtatatt                                                            130

<210> SEQ ID NO 36
<211> LENGTH: 131
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (59)..(69)
<223> OTHER INFORMATION: n is a, c, g, or t
<220> FEATURE:
<221> NAME/KEY: misc_feature
<222> LOCATION: (72)..(77)
<223> OTHER INFORMATION: n is a, c, g, or t
<220> FEATURE:
<221> NAME/KEY: misc_feature
<222> LOCATION: (79)..(81)
<223> OTHER INFORMATION: n is a, c, g, or t
<220> FEATURE:
<221> NAME/KEY: misc_feature
<222> LOCATION: (83)..(87)
<223> OTHER INFORMATION: n is a, c, g, or t
<220> FEATURE:
<221> NAME/KEY: misc_feature
<222> LOCATION: (90)..(95)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 36
aatgatacgg cgaccaccga gatctacact ctttccctac acgacgctct tccgatctnn      60 nnnnnnnna annnnnnann nannnnnaan nnnnnanaga tcggaagagc tcgtatgccg     120
tcttctgctt g                                                          131
```

```
<210> SEQ ID NO 37
<211> LENGTH: 136
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(45)
<223> OTHER INFORMATION: n is a, c, g, or t
<220> FEATURE:
<221> NAME/KEY: misc_feature
<222> LOCATION: (49)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t

<400> SEQUENCE: 37
caagcagaag acggcatacg agctcttccg atctnntnnn nnnnntttnn nntnntnnaa      60
aaaaaaaaaa aaaaaaaaag atcggaagag cgtcgtgtag ggaaagagtg tagatctcgg     120
tggtcgccgt atcatt                                                    136

<210> SEQ ID NO 38
<211> LENGTH: 136
<212> TYPE: DNA
<213> ORGANISM: Artificial sequence
<220> FEATURE:
<223> OTHER INFORMATION: synthetic polynucleotide sequence
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (85)..(88)
<223> OTHER INFORMATION: n is a, c, g, or t
<220> FEATURE:
<221> NAME/KEY: misc_feature
<222> LOCATION: (92)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t

<400> SEQUENCE: 38
aatgatacgg cgaccaccga gatctacact ctttccctac acgacgctct tccgatcttt      60
tttttttttt ttttttttnn annannnnaa annnnnnnna nnagatcgga agagctcgta    120
tgccgtcttc tgcttg                                                   136

<210> SEQ ID NO 39
<211> LENGTH: 33
<212> TYPE: DNA
<213> ORGANISM: Artificial sequence
<220> FEATURE:
<223> OTHER INFORMATION: synthetic polynucleotide sequence
```

```
<400> SEQUENCE: 39
acactctttc cctacacgac gctcttccga tct                           33
```